US008961926B2

(12) United States Patent
Low et al.

(10) Patent No.: US 8,961,926 B2
(45) Date of Patent: Feb. 24, 2015

(54) METHOD OF IMAGING LOCALIZED INFECTIONS

(75) Inventors: Philip Stewart Low, West Lafayette, IN (US); Walter Anthony Henne, Jr., Lafayette, IN (US); Bindu Varghese, Hopewell Junction, NY (US); Ryan Rothenbuhler, Kimmell, IN (US)

(73) Assignee: Purdue Research Foundation, West Lafayette, IN (US)

( * ) Notice: Subject to any disclaimer, the term of this patent is extended or adjusted under 35 U.S.C. 154(b) by 876 days.

(21) Appl. No.: 12/601,960

(22) PCT Filed: May 23, 2008

(86) PCT No.: PCT/US2008/064711
§ 371 (c)(1),
(2), (4) Date: Sep. 28, 2010

(87) PCT Pub. No.: WO2008/148001
PCT Pub. Date: Dec. 4, 2008

(65) Prior Publication Data
US 2011/0044897 A1    Feb. 24, 2011

Related U.S. Application Data

(60) Provisional application No. 60/931,753, filed on May 25, 2007.

(51) Int. Cl.
*A61K 51/00* (2006.01)
*A61K 51/04* (2006.01)

(52) U.S. Cl.
CPC .............................. *A61K 51/0459* (2013.01)
USPC ........... 424/1.61; 424/9.1; 424/9.3; 424/9.36; 424/9.4; 424/9.51; 424/9.42; 424/9.5

(58) Field of Classification Search
CPC ............ A61K 51/0459; A61K 51/025; A61K 49/0004; A61K 49/001
See application file for complete search history.

(56) References Cited

U.S. PATENT DOCUMENTS

| | | |
|---|---|---|
| 2,816,110 A | 12/1957 | Sletzinger et al. |
| 4,577,636 A | 3/1986 | Spears |
| 4,641,650 A | 2/1987 | Mok |
| 4,713,249 A | 12/1987 | Schroder |
| 4,718,417 A | 1/1988 | Kittrell et al. |
| 4,785,806 A | 11/1988 | Deckelbaum |
| 4,817,601 A | 4/1989 | Roth et al. |
| 4,850,351 A | 7/1989 | Herman et al. |
| 4,917,084 A | 4/1990 | Sinofsky |
| 4,950,266 A | 8/1990 | Sinofsky |
| 5,094,848 A | 3/1992 | Brixner |
| 5,108,921 A | 4/1992 | Low et al. |
| 5,140,104 A | 8/1992 | Coughlin et al. |
| 5,192,525 A | 3/1993 | Yang et al. |
| 5,217,456 A | 6/1993 | Narciso |
| 5,266,333 A | 11/1993 | Cady et al. |
| 5,275,594 A | 1/1994 | Baker et al. |
| 5,336,506 A | 8/1994 | Josephson et al. |
| 5,373,093 A | 12/1994 | Vallarino et al. |
| 5,399,338 A | 3/1995 | Born et al. |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,562,100 A | 10/1996 | Kittrell et al. |
| 5,576,305 A | 11/1996 | Ratcliffe |
| 5,688,488 A | 11/1997 | Low et al. |
| 5,753,631 A | 5/1998 | Paulson et al. |
| 5,759,546 A | 6/1998 | Weinberg et al. |
| 5,820,847 A | 10/1998 | Low et al. |
| 6,093,382 A | 7/2000 | Wedeking et al. |
| 6,167,297 A | 12/2000 | Benaron |
| 6,204,371 B1 | 3/2001 | Levinson |
| 6,217,847 B1 | 4/2001 | Contag et al. |
| 6,221,334 B1 | 4/2001 | Wedeking et al. |
| 6,246,901 B1 | 6/2001 | Benaron |
| 6,270,766 B1 | 8/2001 | Feldman et al. |
| 6,335,434 B1 | 1/2002 | Guzaev et al. |
| 6,365,362 B1 | 4/2002 | Terstappen et al. |
| 6,387,350 B2 | 5/2002 | Goldenberg |
| 6,507,747 B1 | 1/2003 | Gowda et al. |
| 6,780,984 B2 | 8/2004 | Wang et al. |
| 6,782,289 B1 | 8/2004 | Strauss |

(Continued)

FOREIGN PATENT DOCUMENTS

| | | |
|---|---|---|
| CA | 2520406 | 10/2004 |
| CA | 2666234 | 5/2008 |

(Continued)

OTHER PUBLICATIONS

Shoup et al (Shoup T M et al: "Synthesis of Fluorine-18-Labeled Biotin Derivatives: Biodistribution and Infection Localization"Journal of Nuclear Medicine, Society of Nuclear Medicine, Reston, VA, US, vol. 35, No. 10, Oct. 1, 1994, pp. 1685-1690, XP000606675,1SSN: 0161-5505).*
XPOO2569963; "Osteomyelitis" XPOO2569963, Retrieved from the Internet:URL:http://emedicine,medscape.com/article/785020-overview.*
Barnes, H. H., et al., "Purification of Catechol Siderophores by Boronate Affinity Chromatography: Identification of Chrysobactin From *Erwinia carotovora subsp. carotovora*", 1999, *BioMetals*, vol. 12, pp. 83-87.
Collins, Peter, et al., "Monosaccharides, Their Chemistry and Their Roles in Natural Products", 1995 *Wiley Publishers*, Book Reference, We will provide a copy of the book if requested.

(Continued)

*Primary Examiner* — Suzanne Ziska
(74) *Attorney, Agent, or Firm* — Barnes & Thornburg LLP

(57) ABSTRACT

The invention relates to a method for targeting an imaging agent to cells of an animal to detect localized infections. More particularly, localized infections are detected by targeting imaging agents to inflammatory cells having receptors for a vitamin by using vitamin-imaging agent conjugates.

19 Claims, 8 Drawing Sheets

(56) References Cited

U.S. PATENT DOCUMENTS

| | | |
|---|---|---|
| 6,960,449 B2 | 11/2005 | Wang et al. |
| 7,033,594 B2 | 4/2006 | Low et al. |
| 7,128,893 B2 | 10/2006 | Leamon et al. |
| 7,223,380 B2 | 5/2007 | Yang et al. |
| 7,381,535 B2 | 6/2008 | Perez et al. |
| 7,601,332 B2 | 10/2009 | Vlahov |
| 8,383,354 B2 | 2/2013 | Low |
| 8,388,977 B2 | 3/2013 | Low et al. |
| 2001/0031252 A1 | 10/2001 | Low et al. |
| 2002/0127181 A1 | 9/2002 | Edwards et al. |
| 2002/0192157 A1* | 12/2002 | Low et al. ............ 424/1.49 |
| 2003/0086900 A1* | 5/2003 | Low et al. ............ 424/85.2 |
| 2003/0162234 A1 | 8/2003 | Jallad et al. |
| 2003/0198643 A1 | 10/2003 | Lu |
| 2003/0219375 A1 | 11/2003 | Piwnica-Worms |
| 2004/0033195 A1 | 2/2004 | Leamon et al. |
| 2004/0057900 A1 | 3/2004 | Edwards et al. |
| 2004/0136910 A1 | 7/2004 | Kennedy et al. |
| 2004/0184990 A1 | 9/2004 | Larsen et al. |
| 2004/0242582 A1 | 12/2004 | Green et al. |
| 2005/0002942 A1 | 1/2005 | Vlahov et al. |
| 2005/0026866 A1 | 2/2005 | Pawelek |
| 2005/0227985 A9 | 10/2005 | Green et al. |
| 2005/0244336 A1 | 11/2005 | Low |
| 2006/0002891 A1 | 1/2006 | Pouletty |
| 2006/0067946 A1 | 3/2006 | Low et al. |
| 2006/0134002 A1 | 6/2006 | Lin |
| 2006/0182687 A1* | 8/2006 | Yang et al. ............ 424/9.364 |
| 2006/0204565 A1 | 9/2006 | Low et al. |
| 2007/0009434 A1 | 1/2007 | Low et al. |
| 2007/0031334 A1* | 2/2007 | Leamon et al. ............ 424/1.69 |
| 2007/0231266 A1 | 10/2007 | Low et al. |
| 2007/0276231 A1 | 11/2007 | Low et al. |
| 2008/0119475 A1 | 5/2008 | Low et al. |
| 2008/0138396 A1 | 6/2008 | Low et al. |
| 2008/0254499 A1 | 10/2008 | Low |
| 2009/0012009 A1 | 1/2009 | Low et al. |
| 2010/0055735 A1 | 3/2010 | Low |
| 2010/0322854 A1 | 12/2010 | Low et al. |
| 2012/0003151 A1 | 1/2012 | Low et al. |
| 2012/0276191 A1 | 11/2012 | Low et al. |
| 2013/0101519 A1 | 4/2013 | Low |

FOREIGN PATENT DOCUMENTS

| | | |
|---|---|---|
| EP | 0220030 | 10/1986 |
| EP | 0273085 | 12/1986 |
| EP | 1940473 | 7/2008 |
| JP | 2774378 | 2/1998 |
| JP | 2004-530678 | 11/2002 |
| JP | 2003-515570 | 5/2003 |
| JP | 2005-519078 | 9/2003 |
| RU | 21 23338 | 11/1996 |
| RU | 2101703 | 10/1998 |
| WO | 90/01296 | 10/1990 |
| WO | 91/19501 | 12/1991 |
| WO | 91/19502 | 12/1991 |
| WO | 92/13572 | 2/1992 |
| WO | WO 96/22521 | 7/1996 |
| WO | 96/36367 | 11/1996 |
| WO | 97/37690 | 10/1997 |
| WO | 98/49196 | 11/1998 |
| WO | 99/41285 | 8/1999 |
| WO | 00/73332 | 12/2000 |
| WO | 01/19320 | 3/2001 |
| WO | 01/39806 | 6/2001 |
| WO | WO 01/47552 | 7/2001 |
| WO | 01/74382 | 10/2001 |
| WO | 01/91807 | 12/2001 |
| WO | 02/087424 | 11/2002 |
| WO | WO 03/072091 | 9/2003 |
| WO | 2004/044227 | 5/2004 |
| WO | 2004/069159 | 8/2004 |
| WO | 2004/110250 | 12/2004 |
| WO | 2005/049579 | 6/2005 |
| WO | 2005/067644 | 7/2005 |
| WO | 2005/087275 | 9/2005 |
| WO | WO2006/012527 A | 2/2006 |
| WO | WO 2006/034046 | 3/2006 |
| WO | WO 2006/065943 | 6/2006 |
| WO | WO 2006/071754 * | 7/2006 |
| WO | WO2006/071754 A | 7/2006 |
| WO | 2006/101845 | 9/2006 |
| WO | 2007/001466 | 1/2007 |
| WO | 2007/006041 | 1/2007 |
| WO | WO 2007/006041 * | 1/2007 |
| WO | 2007/038346 | 4/2007 |
| WO | 2008/057437 | 5/2008 |
| WO | 2008/098112 | 8/2008 |
| WO | 2008/148001 | 12/2008 |
| WO | 2009/002993 | 12/2008 |
| WO | WO 2009/026177 | 2/2009 |

OTHER PUBLICATIONS

Georgakoudi, Irene, et al., "In Vivo Flow Cytometry: A New Method for Enumerating Circulating Cancer Cells", Aug. 1, 2004, *Cancer Research*, No. 64, pp. 5044-5047.

Hanessian, Stephen, "Preparative Carbohydrate Chemistry", 1997 *Marcel Dekker, Inc.*, Book Reference, We will provide a copy of the book if requested.

Idanpaan-Heikkila, Ilona, et al., "Oligosaccharides Interfere With the Establishment and Progression of Experimental Pneumococcal Pneumonia", 1997, *The Journal of Infectious Diseases*, No. 176, pp. 704-712.

Iijima, Masatomi, et al., "IC202A, A New Siderophore With Immunosuppressive Activity Produced by *Streptoalloteichus* sp. 1454-19. I. Taxonomy, fermentation, isolation and biological activity.", Jan. 1999, *The Journal of Antibiotics* (Toyko), vol. 52, No. 1, pp. 20-24.

Lingwood, Clifford A., "Oligosaccharide Receptors for Bacteria: A View to a Kill", 1998, *Curr Opin Chem Biol.*, pp. 695-700.

Michelson, Alan D., et al "Evaluation of Platelet Function by Flow Cytometry", 2000, Methods, vol. 21, pp. 259-270.

Novak, J., et al., "In Vivo Flow Cytometer for Real-Time Detection and Quantification of Circulating Cells", Jan. 1, 2004 *Optics Letters*, vol. 29, No. 1, pp. 77-79.

Ratledge, Colin, et al., "The Occurrence of Carboxymycobactin, The Siderophore of Pathogenic Mycobacteria, As a Second Extracellular Siderophore in *Mycobacterium smegmatis*", 1996 *Microbiology*, vol. 142, pp. 2207-2212.

Scharfman, Andree, et al., "*Pseudomonas aeruginosa* Binds to Neoglycoconjugates Bearing Mucin Carbohydrate Determinants and Predominantly to sialyl-Lewis x Conjugates", 1999, *Glycobiology*, vol. 9, No. 8, pp. 757-764.

Albrecht-Gary et al., "Bacterial Iron Transport: Coordination Properties of Pyoverdin PaA, a Peptidic Siderophore of *Pseudomonas aeruginosa*", 1994. *Inorg. Chenz.*, 33 (26), pp. 6391-6402.

Henne, Walter A., et al., "Synthesis and Activity of a Folate Peptide Camptothecin Prodrug", (Aug. 9, 2006), *Bioorganic & Medicinal Chemistry Letters*, vol. 16, pp. 5350-5355.

Tang, Hailun, et al., "Prostate Targeting Ligands Based on N-Acetylated α-Linked Acidic Dipeptidase", (2003), *Biochemical and Biophysical Research Communications*, vol. 307, pp. 8-14.

Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp. 1917-1926.

Schalk, Isabelle J., et al., "iron-Free Pyoverdin Binds to Its Outer Membrane Receptor FpvA in *Pseudomonas aeruginosa*: A New Mechanism for Membrane Iron Transport", 2001, *Molecular Microbiology*, vol. 39, No. 2, pp. 351-360.

Wiener et al., "Targeting Dendrimer-Chelates to Tumors and Tumor Cells Expressing the High-Affinity Folate Receptor," *Investigative Radiology*, 1997; 32(12):748-754.

Paulos et al., "Ligand Binding and Kinetics of Folate Receptor Recycling in Vivo: Impact on Receptor-Mediated Drug Delivery," *Molecular Pharmacology*, 2004; 66:1406-1414.

(56) References Cited

OTHER PUBLICATIONS

"Osteomyelitis", XP-002569963, URL:http://emedicine.medscape.com/article/785020-overview>, retrieved Feb. 22, 2010.
International Search Report for PCT/US2008/064711, dated Mar. 5, 2010.
Kennedy MD, "Folate-targeted imaging agents," Thesis submitted to the faculty of Purdue University in partial fulfillment of the requirements for the degree of Doctor of Philosophy, published Nov. 2004.
Holladay et al., "Riboflavin-mediated delivery of a macromolecule into cultured human cells," Biochitn Biophys Acta 1426(1): 195-204 (1999).
Kennedy et al., "Optical imaging of metastatic tumors using a folate-targeted fluorescent probe," J. of Biomedical Optics, vol. 8, No. 4, pp. 636-641, Oct. 2003.
Low PS, Leamon CP, Reddy JA, Green MA, Mathias C, Turk MJ, Waters DJ, Lu J, Lee RJ, Kennedy MD, "Folate-mediated delivery of therapeutic and imaging agents to cancer tissue," Gene, Drug Therapy, and Molecular Biology (Abstract), 2000.
Low, P.S., Leamon, C.P., Reddy, J.A., Green, M.A., Mathias, C., Turk, MJ., Waters, D.J., Lu, J., Lee, R.J. and Kennedy, M., "Folate-Mediated Delivery of Therapeutic and Imaging Agents to Cancer Tissues In Vivo," International Symposium on Tumor Targeted Delivery Systems, Bethesda, Maryland. British Journal of Pharmacology, vol. 134 (Abstract), 2001.
International Search Report/Written Opinion prepared for PCT/US2008/064711, received May 27, 2010.
King, Randall W., et al., "Osteomyelitis", Retrieved from the Internet: URL:http//emedicine.medscape.com/article/78520-overview.
Achilefu et al., "Novel Receptor-Targeted Fluorescent Contrast Agents for In Vivo Tumor Imaging", Investigative Radiology, vol. 35, No. 8, pp. 479-485, Aug. 2000.
Antohe et al., "Increased uptake of folate conjugates by activated macrophages in experimental hyperlipemia", Cell Tissue Research, vol. 320, No. 2, pp. 277-285, May 2005.
Aviram et al., "Intralipid infusion abolishes ability of human serum to cholesterol-load cultured macrophages", Arteriosclerosis, vol. 9, pp. 67-75, 1989.
Ballou et al., "Tumor labeling in vivo using cyanine-conjugated monoclonal antibodies", Cancer Immunol Immunother, vol. 41, pp. 257-263, 1995.
Barrera et al., "Synovial macrophage depletion with clodronate-containing liposomes in rheumatoid arthritis", Arthritis and Reheumatism, vol. 43, pp. 1951-1959, Sep. 2000.
Beaumont et al., "Selective Fluorodenitration of Chloronitroaromatics", J. Fluorine Chem., vol. 63, pp. 25-30, 2003.
Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.
Bettio et al., "Synthesis and Preclinical Evaluation of a Folic Acid Derivative Labeled with 18F for PET Imaging of Folate Receptor-Positive Tumors", The Journal of Nuclear Medicine, vol. 47, No. 7, pp. 1153-1160, Jul. 2006.
Bock et al., "Sulfonamide Structure-Activity Relationships in a Cell-Free System. 2 Proof for the Formation of a Sulfonamide-Containing Folate Analog", Journal of Medicinal Chemistry, vol. 17, No. 1, pp. 23-28, 1974.
Boechat et al., "Fluorodenitrations Using Tetramethylammonium Fluoride", J. Soc. Chem, Commun., pp. 921-92, 1993.
Boente et al., "Screening, imaging, and Early Diagnosis of Ovarian Cancer", Clinical Obstetrics and Gynecology, vol. 37, No. 2, pp. 377-391, Jun. 1994.
Budinger et al., "New Approaches to Targeting Arthritis with Radiopharmaceuticals", The Journal of Rheumatology, 22(1) Supp: 62-67, 1995.
Campbell et al., "Folate-binding Protein is a Marker for Ovarian Cancer", Cancer Research, vol. 51, pp. 5329-5338, Oct. 1, 1991.

Canis et al., "Lapascopic Diagnosis of Adnexal Cystic Masses: A 12-Year Experience With Long-Term Follow-Up", Obstetrics & Gynecology, vol. 83, No. 5, pp. 707-712, May 1994.
Case, "Ultrasound Physics and Instrumentation", Surgical Clinics of North America, vol. 78, No. 2, pp. 197-217, Apr. 1998.
Chen et al., "MicroPET Imaging of Brain Tumor Angiogenesis with 18F-Labeled PEGylated RGD Peptide", European Journal of Nuclear Medicine and Molecular Imaging, vol. 31, No. 8, pp. 1081-1089, Aug. 2004.
Tung et al., "Preparation of a Cathepsin D Sensitive Near-Infrared Fluorescence Probe for Imaging", American Chemical Society, vol. 10, No. 5, pp. 692-696, Sep. 20, 1999.
Cohen et al., "Screening for ovarian cancer: The role of noninvasive imaging techniques", Am J. Obstet Gynecol., vol. 170, No. 4, pp. 1088-1094, 1994.
Cohen et al., "Three-Dimensional Power Doppler Ultrasound Improves the Diagnostic Accuracy for Ovarian Cancer Prediction", Gynecologic Oncology, vol. 82, pp. 40-48, 2001.
Cox et al., "Anhydrous, Tetrabutylammonium Fluoride: A Mild but Highly Efficient Source of Nucleophilic Fluoride Ion", J. Org. Chem., No. 49, pp. 3216-3219, 1984.
DePriest et al., "Transvaginal Sonography as a Screening Method for the Detection of Early Ovarian Cancer", Gynecologic Oncology, vol. 65, No. GO974705, pp. 408-414, 1997.
Feldman et al., "Anti-TNFa Therapy Is Useful in Rheumatoid Arthritis and Crohn's Disease: Analysis of the Mechanism of Action Predicts Utility in Other Diseases", Transplant. Proc., 30, pp. 4126-4127, 1998.
Forstner et al., "CT and MRI of ovarian cancer", Abdominal Imaging, vol. 20, pp. 2-8, 1995.
Garg et al., "Fluorine-18 Labeling of Monoclonal Antibodies and Fragments with Preservation of Immunoreactivity", Bioconjugate Chem., vol. 2, No. 1, pp. 44-49, 1991.
U.S. Appl. No. 61/235,220, filed Aug. 19, 2009, Low et al.
U.S. Appl. No. 61/157,847, filed Mar. 5, 2009, Low et al.
Giroldo et al., An Unusually Fast Nucleophilic Aromatic Displacement Reaction: The Gas-Phase Reaction of Fluoride Ions with Nitrobenzene, Angew. Chem. Int. Ed., No. 43, pp. 3588-3590, 2004.
Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, 1972.
Gotoh, "Causes and treatment of rheumatoid arthritis; recent trend I. Progress in pathogenesis of rheumatoid arthritis; role of macrophages and dendritic cells", Pharma Nedica, Japan Medical Review Co., Ltd., Tokyo, 17(10): 35-39, 1999.
Greenman et al., "Heterogeneous Expression of Two Somatostatin Receptor Subtypes in Pituitary Tumors," Journal of Clinical Endocrinology and Metabolism, vol. 78, No. 2, pp. 398-403, 1994.
Hamacher et al., "No-Carrier-Added Nucleophilic 18F-Lavelling in an Electrochemical Cell Exemplified by the Routine Production of [18F]altanserin", Applied Radiation and Isotopes, No. 64, pp. 989-994, 2006.
Harris et al., "Human leukemic models of myelomonocytic development: a review of the HL-60 and U937 cell lines", Journal of Leukocyte Biology, vol. 37, No. 4, pp. 407-422, 1985.
Holmgren et al. "Strategies for the Induction of Immune Responses at Mucosal Surfaces Making Use of Cholera Toxin B Subunit As Immunogen, Carrier, and Adjuvan"t, Am. J. Trop Med Hyd, 50, pp. 42-54, 1994.
Hynes et al., "Quinazolines as Inhibitors of Dihydrofolate Reductase. 4. Classical Analogues of Folic and Isofolic Acids", Journal of Medicinal Chemistry, vol. 20, No. 4, pp. 588-591, 1977.
Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.
Johnstrom et al., "18F-Endothelin-1, a Positron Emission Tomography (PET) Radioligand for the Endothelin Receptor System: Radiosynthesis and In Vivo Imaging Using MicroPET", Clinical Science, vol. 103, Suppl. 48, pp. 45-85, 2003.

(56) References Cited

OTHER PUBLICATIONS

Karlan, "The Status of Ultrasound and Color Doppler Imaging for the Early Detection of Ovarian Cancer", Cancer Investigation, vol. 15, No. 3, pp. 265-269, 1997.
Karlan et al., "Ovarian Cancer Screening: The Role of Ultrasound in Early Detection", Cancer Supplement, vol. 76, No. 10, pp. 2011-2015, Nov. 15, 1995.
Karsten et al., "Towards Usage-Based Accounting: Applying Policy-Based Intelligent Agents, ITC 15" Elsevier Science B.V., pp. 633-642, 1997.
Kennedy et al., "Evaluation of Folate Conjugate Uptake and Transport by the Choroid Plexus of Mice", Pharmaceutical Research, vol. 20, No. 5, p. 714-719, May 2003.
Kennedy et al., "Optical imaging of metastatic tumors using a folate-targeted fluorescent probe", J. of Biomedical Optics, vol. 8, No. 4, pp. 636-641, Oct. 2003.
Kim et al., "Synthesis and Biological Activity of 10-Thia-10-deaza Analogs of Folic Acid, Pteroic Acid, and Related Compounds", Journal of Medicinal Chemistry, vol. 18, No. 8, pp. 776-780, 1975.
Kinne et al., "Macrophage in rheumatoid arthritis", Arthritis Research, vol. 2, No. 3, pp. 189-202, 2000.
Konda et al., "Development of a Tumor-Targeting MR Contrast Agent Using the High-Affinity Folate Receptor", Investigative Radiology, vol. 35, No. 1, pp. 50-57, 2000.
U.S. Appl. No. 12/526,096, filed Aug. 6, 2009, Low et al.
Kramer, "Basic Principles of Magnetic Resonance Imaging", Radiological Clinics of North America, vol. 22, No. 4, pp. 765-778, Dec. 1984.
Kuriowa et al., "Development of a Fluorescein Operative Microscope for Use During Malignant Glioma Surgery", Elsevier Science Inc., vol. 50, pp. 41-49, 1998.
Leamon et al., "Folate-mediated targeting: from diagnosis to drug and gene therapy" DDT vol. 6 No. 1 44-51, Jan. 2001.
Leamon et al., "Synthesis and Biological Evaluation of EC140: A Novel Folate—Targeted Cinca Alkaloid Conjugate", Bioconjugate Chem., vol. 17, No. 5, pp. 1226-1232, 2006.
Leamon et al., "Synthesis and Biologicial Evaluation of EC20: A New Folate-Derived, 99mTc-Based Radiopharmaceutical" Bioconjugate Chemistry, vol. 13, No. 6, pp. 1200-1210, 2002.
Leamon et al., "Selective Targeting of Malignant Cells with Cytotoxin-Folate Conjugates", J. Drug Targeting 2: 101-112, 1994.
Lee et al., "Folic Acid Antagonists. Methotrexate Analogs Containing Spurious Amino Acids. Dichlorohomofolic Acid" Journal of Medicinal Chemistry, vol. 17, No. 3, pp. 326-330, 1974.
Lemaire et al., "Fluorine-18-Altanserin: A Radioligand for the Study of Serotonin Receptors with PET: Radiolabeling and In Vivo Biologic Behavior in Rats", The Journal of Nuclear Medicine. vol. 32, No. 12, pp. 2266-2272, Dec. 1991.
Licha et al., "Hydrophilic Cyanine Dyes as Contrast Agents for Near-infrared Tumor Imaging: Synthesis, Photophysical Properties and Spectroscopic In vivo Characterization, Photochemistry and Photobiology", vol. 72, No. 3, pp. 392-398, 2000.
Liotta et al., "The Chemistry of "Naked" Anions. I. Reactions of the 18-Crown-6 Complex of Potassium Fluoride with Organic Substrates in Aprotic Organic Solvents", Journal of American Chemical Society, vol. 96, No. 7, pp. 2250-2252, Apr. 3, 1974.
Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.
Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, No. 2, pp. 391-400, 1995.
Lu et al., "Folate-Targeted Enzyme Prodrug Cancer Therapy Utilizing Penicillin-V Amidase and a Doxorubicin Prodrug" J. Drug Targeting 7:43-53, 1999.
Mahmood et al., "Near Infrared Optical Imaging for Protease Activity for Tumor Detection", Radiology, 213:866-870, 1999.
Maiman et al., "Laproscopic Excision of Ovarian Neoplasm Subsequently Found to Be Malignant", Obstetrics & Gynecology, vol. 77, No. 4, pp. 563-565, Apr. 1991.
Mancini et al., "Relative contributions of apolipoprotein A and apolipoprotein B to the development of fatty lesions in the proximal aorta of mice", Arterioscler. Thromb. Vasc. Biol., vol. 15, pp. 1911-1916, 1995.
Mantovani et al., "Folate Binding Protein Distribution in Normal Tissues and Biological Fluids From Ovarian Carcinoma Patients as Detected by the Monoclonal Antibodies Mov 18 and Mov 19", European Journal of Cancer, vol. 30A, No. 3, pp. 363-369, 1994.
Matsuyama et al., Clinical significance of the folate receptor beta expression in rheumatoid synovial macrophages, Rheumatoid, Japan College of Rheumatology, 41(2): 265, 2001.
Matsuyama et al., "Activation and pathological significance of macrophages in rheumatoid synovitis" Clinical Immunity, Japan, Kagaku Hyoronsha, Tokyo, 30(2): 214-219, 1998.
Mestas et al., Of Mice and Not Men: Differences between Mouse and Human Immunology, J. of Immunology, 172, pp. 2731-2738, 2004.
Mukasa et al., "Function analysis of folate receptorβ in a RA synovial membrane macrophage cell line" Rheumatoid, Japan College of Rheumatology, 40(2): 378, 2000.
Mulherin et al., "Synovial tissue macrophage populations and articular damage in rheumatoid arthritis", Arthritis and Rheumatism, vol. 39, No. 1, pp. 115-124, 1996.
Murakami et al., "18F-Labelled Annexin V: A PET Tracer for Apoptosis Imaging", European Journal of Nuclear Medicine and Molecular Imaging, vol. 31, No. 4, pp. 469-474, Apr. 2004.
Nagayoshi et al., "Arthritis and Reheumatism", vol. 52, pp. 2666-2675, Sep. 9, 2005.
Nair et al., "Folate Analogues Altered in the C9-N10 Bridge Region. 10-Oxafolic Acid and 10-Oxaaminopterin", Journal of Medicinal Chemistry, vol. 19, No. 6, pp. 825-829, 1976.
Nair et al., "Folate Analogues Altered in the C9-N10 Bridge Region: N10-Tosylisohomofolic Acid and N10-Tosylisohomoaminopterin", Journal of Medicinal Chemistry, vol. 21, No. 7, pp. 673-677, 1978.
Nair et al., "Folate Analogues Altered in the C9-N10 Bridge Region: 11-Thiohomofolic Acid", Journal of Medicinal Chemistry, vol. 22, No. 7, pp. 850-855, 1979.
Nair et al., "Folate Analogues Altered in the C9-N10 Bridge Region. 14. 11-Oxahomofolic Acid, a Potential Antitumor Agent", Journal of Medicinal Chemistry, vol. 23, pp. 59-65, 1980.
Nair et al., Folate Analogues Altered in the C9-N10 Bridge Region. 18. Synthesis and Antitumor Evaluation of 11-Oxahomoaminopterin and Related Compounds, Journal of Medicinal Chemistry, vol. 24, pp. 1068-1073, 1981.
Nair et al., "Folate Analogues. 20. Synthesis and Antifolate Activity of 1, 2, 3, 4, 5, 6,—Hexahydrohomofolic Acid", Journal of Medicinal Chemistry, vol. 26, pp. 135-140, 1983.
Nair et al., "Folate Analogues. 21. Synthesis and Antifolate and Antitumor Activities of N10-(Cyanomethyl)-5,8-dideazafolic Acid", Journal of Medicianal Chemistry, vol. 26, pp. 605-607, 1983.
Nair et al., "Folate Analogues. 22. Synthesis and Biological Evaluation of Two Analogues of Dihydrofolic Acid Processing a 7,8-Dihydro-8-oxapterin Ring System" Journal of Medicinal Chemistry, vol. 26, 1164-1168, 1983.
Nakashima-Matsushita et al., Selective expression of folate receptor beta and its possible role in methotrexate transport in synovial macrophages from patients with rheumatoid arthritis, Arthritis Rheum. 42(8): 1609-1616, 1999.
Nezhat et al., "Four ovarian cancers diagnosised during laproscopic management of 1011 women with adnexal masses", Am J Obstet Gynecol., vol. 167, No. 3, pp. 790-796, 1992.
Oatis et al., "Synthesis of Quinazoline Analogues of Folic Acid Modified at Position 10", Journal of Medicinal Chemistry, vol. 20, No. 11, pp. 1393-1396, 1977.
Olma et al., "4-[18F]fluorophenyl ureas via carbamate-4-nitrophenyl esters and 4-[18F]Fluoroaniline", Journal of Labeled Compd. and Radiopnarm, vol. 49, pp. 1037-1050, 2006.
Paigen et al., "Variation in susceptibility to atherosclerosis among inbred strains of mice", Atherosclerosis, vol. 57, No. 1, pp. 65-73, 1985.

(56) References Cited

OTHER PUBLICATIONS

Pasterkamp et al., "Techniques characterizing the coronary atherosclerotic plaque: Influence on clinical decision making?", J. Amer. Coll. Cardiol. 36:13-21, 2000.
Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.
Plante et al., "Polyglutamyl and Polylysyl Derivatives of the Lysine Analogues of Folic Acid and Homofolic Acid", Journal of Medicinal Chemistry, vol. 19, No. 11, pp. 1295-1299, 1976.
Rampone et al., "Ovarian cancer screening by transvaginal color Doppler ultrasonography", Minerva Ginecologica, vol. 53, Suppl. 1 al N 1, pp. 125-128, 2001.
Reddy et al., "Optimization of Folate-Conjugated Liposomal Vectors for Folate Receptor-Mediated Gene Therapy", J. Pharm. Sciences 88: 1112-1118, 1999.
Reddy et al., "Folate-Mediated Targeting of Therapeutic and Imaging Agents to Cancers", Critical Reviews In Ther. Drug Carrier Systems 15: 587-627, 1998.
Reddy et al., "Folate receptor specific anti-tumor activity of folate-mitomycin conjugates", Cancer Chemother. Pharmacol., 58(2): 229-36, 2006.
Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.
Roberts et al., "Folic Acid Analogs. Modifications in the Benzene-Ring Region. 3. Neohomofolic and Neobishomofolic Acids. An Improved Synthesis of Folic Acid and Its Analogs". Journal of Medicinal Chemistry, 16(6): 697-699, 1973.
Roberts et al., "Folic Acid Analogs. Modifications in the Benzene-Ring Region. 2. Thiazole Analogs", Journal of Medicinal Chemistry, 15 (12): 1310-1312, 1972.
Roberts et al., "Folic Acid Analogs. Modifications in the Benzene-Ring Region. 1. 2'- and 3'- Azafolic Acids", Journal of Medicinal Chemistry, 14(2): 125-130, 1971.
Roberts et al., "Folic Acid Analogs. Modifications in the Benzene-Ring Region. 4. 3'- Ethyl—and 3'- Isopropylfolic Acids", Journal of Medicinal Chemistry, vol. 17, No. 2, pp. 219-222, 1974.
Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.
Sato et al., "Usefulness of Mass Screening for Ovarian Carcinoma Using Transvaginal Ultasonography", American Cancer Society, vol. 89, No. 3, pp. 582-588, 2000.
Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-64, 1997.
Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Feb. 2000.
Sijtsema et al., "Confocal Direct Imaging Raman Microscope: Design and Application in Biology", Applied Spectroscopy, vol. 52, Issue 3, pp. 348-355, 1998.
Sima et al., "Experimental obstructive coronary atherosclerosis in the hyperlipidemic hamster", J Submicrosc Cytol Pathol, vol. 22, No. 1, pp. 1-16, 1990.
Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16. 1990.
Smart et al., "Protein kinase C activators inhibit receptor-mediated potocytosis by preventing internalization of caveolae", Journal of Cell Biology, vol. 124, No. 3, pp. 307-313,1994.
Solomon et al., "Computerized Tomography in Ovarian Cancer", Gynecologic Oncology, vol. 15 pp. 48-55, 1983.
Sudimak et al., "Targeted drug delivery via the folate receptor", Advanced Drug Delivery Reviews,vol. 41, pp. 147-162, 2000.

Sun et al., "Anhydrous Tetrabutylammonium Fluoride", J. Am. Chem. Soc., vol. 127, No. 7, pp. 2050-2051, 2005.
Sun et al., "Room-Temperature Nucleophilic Aromatic Fluorination: Experimental and Theoretical Studies", Angew. Chem. Int. Ed., No. 45, pp. 2720-2725, 2006.
Sundstrum et al., "Establishment and characterization of a human histiocytic lymphoma cell line (U-937)", International Journal of Cancer, vol. 17, No. 5, pp. 565-577, 1976.
Sutcliffe-Goulden, "Solid Phase Synthesis of [18F]Labelled Peptides for Positron Emission Tomography", Bio. & Medicin. Chem. Letters, No. 10, pp. 1501-1503, 2000.
Tan et al., "A Complete Remote-Control System for Reliable Preparation of [18F]altanserin", Applied Radiation and Isotopes, vol. 50, pp. 923-927, 1999.
Temple, Jr., et al., "Synthesis of Pseudo Cofactor Analogues as Potential Inhibitors of the Folate Enzymes", Journal of Medicinal Chemistry, 1982, vol. 25, pp. 161-166, 1982.
Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.
Toffoli et al., "Overexpression of Folate Binding Protein in Ovarian Cancers", Int. J. Cancer (Pred. Oncol.), vol. 74, pp. 193-198, 1997.
Urban, "Screening for ovarian cancer: We now need a definitive randomized trial", BMJ, vol. 319, pp. 1317-1318, Nov. 20, 1999.
Van Noort et al., "Cell Biology of Autoimmune Diseases", International Review of Cytology, vol. 178, pp. 127-204, 1998.
Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.
Wang et al., "Chemokines and their role in cardiovascular diseases", TCM, vol. 8, pp. 169-174, 1998.
Wang et al., "Synthesis, Purification, and Tumor Cell Uptake of Ga-Deferoxamine-Folate, a Potential Radiopharmaceutical for Tumor Imaging", American Chemical Society, Bioconjugate Chem., 7(1): 56-62, 1996.
Weinstock et al., "Folic Acid Analogs. II. p-{[2,6-Diamino-8-purinyl)methyl]amino}—benzoyl-L-glutamic Acid and Related Compounds", Journal of Medicinal Chemistry, 13(5): 995-997, 1970.
Weissleder et al., "In vivo imaging of tumors with protease-activated near-infrared fluorescent probes", Nature Biotechnology, vol. 17, pp. 375-378, 1999.
Weitman et al., "The folate receptor in central nervous system malignancies of childhood", Journal of Neuro-Oncology, vol. 21, pp. 107-112, 1994.
Westerhof et al., "Carrier-and Receptor-Mediated Transport of Folate Antagonists Targeting Folate-Dependent Enzymes: Correlates of Molecular-Structure and Biological Activity", Molecular Pharmacology, 1995, 48: 459-471, 1995.
Whitehurst et al., "Development of an alternative light source to lasers for biomedical applications", SPIE, vol. 2629, pp. 291-298, 1993.
Wu et al., "Expression of Folate Receptor Type a in Relation to Cell Type Malignancy, and Differentiation in Ovary, Uterus and Cervix", Cancer Epidemiology, Biomarkers & Prevention, vol. 8, pp. 775-782, Sep. 1999.
Yavorsky et al., Antiparticles:, Handbook on Physics, pp. 339-340, 1984.
Delaloye et al., "Tumor imaging with monoclonal antibodies", Seminars in Nuclear Medicine, 25:144-164, 1995.
Reubi, "The role of peptides and their receptors as tumor markers", Endocrinology & Metabolism Clinics of North America, 22: 917-939, 1993.
Garin-Chesa et al., "Trophoblast and ovarian cancer antigen LK26. Sensitivity and specificity in immunopathology and molecular identification as a folate-binding protein", American Journal of Pathology, 142: 557-567, 1993.
Patrick et al., "Folate receptors as potential therapeutic targets in choroid plexus tumors of SV40 transgenic mice", Journal of Neuro-Oncology, 32: 111-123, 1997.

(56) References Cited

OTHER PUBLICATIONS

Weitman et al., "Distribution of the folate receptor GP38 in normal and malignant cell lines and tissues", Cancer Research, 52: 3396-3401, 1992.
Mathias et al., "Indium-111-DTPA-folate as a potential folate-receptor-targeted radiopharmaceutical", Journal of Nuclear Medicine, 39: 1579-1585, 1998.
Acosta et al., "Chromoendoscopy—where is it useful?", Journal of Clinical Gastroenterology, 27:13-20,1998.
Fleischer, "Chromoendoscopy and magnification endoscopy in the colon", Gastrointestinal Endoscopy, 49: S45-49, 1999.
Stepp et al., "Fluorescence endoscopy of gastrointestinal diseases: basic principles, techniques, and clinical experience", Endoscopy, 30: 379-386, 1998.
Ballou et al., "Tumor detection and visualization using cyanine fluorochrome-labeled antibodies", Biotechnology Progress, 13: 649-658, 1997.
Licha et al., "Synthesis, characterization, and biological properties of cyanine-labeled somatostatin analogues as receptor-targeted fluorescent probes", Bioconjugate Chemistry, 12: 44-50, 2001.
Becker et al., "Receptor-targeted optical imaging of tumors with near-infrared fluorescent ligands", Nature Biotechnology, 19: 327-331, 2001.
Terpetschnig et al., "Synthesis of squaraine-N-hydroxysuccinimide esters and their biological application as long-wavelength fluorescent labels", Analytical Biochemistry, 217: 197-204, 1994.
Mujumdar et al., "Cyanine dye labeling reagents containing isothiocyanate groups", Cytometry, 10: 11-19, 1989.
Wang et al., "Design and synthesis of [111In]DTPA-folate for use as a tumor-targeted radiopharmaceutical", Bioconjugate Chemistry, 8: 673-679, 1997.
Dimartino et al., "Antiarthritic and immunoregulatory activity of spirogermanium", Journal of Pharmacology an Experimental Therapeutics, 236: 103-110, 1986.
Ross et al., "Differential regulation of folate receptor isoforms in normal and malignant tissues in vivo and in established cell lines. Physiologic and clinical implications", Cancer, 73: 2432-2443, 1994.
Ross et al., "Folate receptor type beta is a neutrophilic lineage marker and is differentially expressed in myeloid leukemia", Cancer, 85: 348-357, 1999.
Curtin et al., "Stage IV ovarian cancer: impact of surgical debulking", Gynecologic Oncology, 64: 9-12, 1997.
Munkarah et al., "Prognostic significance of residual disease in patients with stage IV epithelial ovarian cancer", Gynecologic Oncology, 64: 13-17, 1997.
Murolo et al., "Ultrasound examination in ovarian cancer patients. A comparison with second look laparotomy", Journal of Ultrasound in Medicine, 8: 441-443, 1989.
Piver et al., "Second-look laparoscopy prior to proposed second-look parotomy", Obstetrics and Gynecology, 55: 571, 1980.
Bell et al., "Intraoperative radioimmunodetection of ovarian cancer using monoclonal antibody B72.3 and a portable gamma-detecting probe", Obstetrics and Gynecology, 76: 607-677, 1990.
Reuter et al., "Detection of colorectal carcinomas by intraoperative RIS in addition to preoperative RIS: surgical and immunohistochemical findings", European Journal of Nuclear Medicine, 19: 102-109, 1992.
Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.
Folli et al., "Immunophotodiagnosis of colon carcinomas in patients injected with fluoresceinated chimeric antibodies against carcinoembryonic antigen", Proceedings of the National Academy of Sciences of the United States of America, 89: 7973-7977, 1992.
Folli et al., "Antibody-indocyanin conjugates for immunophotodetection of human squamous cell carcinoma in nude mice", Cancer Research, 54: 2643-2649, 1994.
Bannwarth et al., "Methotrexate in rheumatoid arthritis. An update", Drugs, 47: 25-50, 1994.
Bettegowda, et al., Proc. Natl. Acad. ScL U.S.A., 102: 1145-1150, 2005.
Bunce, et al., Infect. Immun., 60: 2636-2640, 1992.
Claassen E. et al., "Preparation and characteristics of dichloromethylene diphosphonate-containing liposomes," J. Microencapsul., 3: 109-14, 1986.
Marceau et al., Bioorganics and Medical Chemistry Letters, 15(24): 5442-5445, 2005.
Novabiochem® Letters, "Resins for the synthesis of biotinylated and fluorescently-labeled peptides," Jan. 2004, pp. 1-4, 2004.
Novabiochem® Letters, "Products for peptide ligation," Feb. 2004, pp. 1-4, 2004.
Novabiochem® Letters, "Amino acids for Fmoc SPPS," Mar. 2004, pp. 1-4, 2004.
Novabiochem® Letters, "PEG reagents," Apr. 2004, pp. 1-4, 2004.
Bonasera et al., "The Synthesis of [26, 27-11C]Dihydroxyvitamin D3, a Tracer for Positron Emission Tomography (PET), Bioorganic & Medicinal Chemistry", Elsevier Science Ltd., vol. 9, pp. 3123-3128, 2001.
Burke et al., "Book Review. The Macrophage", British Journal of Cancer, vol. 89, p. 421, 2003.
Degrado et al., "Synthesis and Evaluation of (18)F-Labeled Choline Analogs as Oncologic PET Tracers", J. Nuclear Medicine, vol. 42, No. 12, pp. 1805-1814, 2001.
Mathias et al., "Preparation of 66Ga- and 68GA-labeled GA(III)-deferoxamine-folate as potential folatereceptor-targeted PET radiopharmaceuticals", Nuclear Medicine and Biology, vol. 30, pp. 725-731, 2003.
Paulos et al. "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.
Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.
Shoup et al., "Synthesis of Fluorine-18-Labeled Biotin Derivatives: Biodistribution and Infection Localization", J. Nuclear Medicine, vol. 35, No. 10, pp. 1685-1690, 1994.
Turk et al., "Folate-targeted imaging of activated macrophage in rats with adjuvant-induced arthritis", Arthritis and Rheumatism, vol. 46, No. 7, pp. 1947-1955, 2002.
Zeisel at al., "Choline, an Essential Nutrient for Humans", The Faseb Journal, vol. 5, No. 7, pp. 2093-2098, 1991.
Marecos et al., "Antibody-Mediated versus Nontargeted Delivery in a Human Small Cell Lung Carcinoma Model", Bioconjugate Chemistry, 9:184-191 (1998).
U.S. Appl. No. 13/723,350, filed Dec. 21, 2012, Jallad et al.
U.S. Appl. No. 13/723,356, filed Dec. 21, 2012, Jallad et al.
Kern, et al., "Evaluation of the Culprit Plaque and the Physiological Significance of Coronary Atherosclerotic Narrowings," Circulation, 2001; 103:3142-3149.
Kanagaki et al., "Pituitary Gland and Parasellar Region," in *Magnetic Resonance Tomography*, Reiser et al. (eds.), 2008, p. 422.
He et al., "In vivo quantitation of rare circulating tumor cells by multiphoton intravital flow cytometry," Proc Nat Acad Sci USA, 2007; 104: 11760-11765.
Chen et al., "In vivo imaging of proteolytic activity in atherosclerosis," Circulation, 2002, 105: 2766-2771.
Mathias et al., "Synthesis of [99mTc]DTPA-Folate and Its Evaluation as a Folate-Receptor-Targeted Radiopharmaceutical", Bioconj. Chem., 2000; 11:253-257.
Linder et al., "In Virto & In Vivo Studies with α-and y-Isomers of 99mTc-OXA-Folate Show Uptake of Both Isomers in Folate-Receptor (+) KB Cell Lines", Soc. Nucl. Med. Proc., May 2000; 41:5:119.
Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.
Massoud et al., "Molecular imaging in living subjects: seeing fundamental biological processes in a new light", 2003, Genes Dev. 17: 545-580.
Caliceti et al., "Pharmacokinetic and biodistution properties of poly9ethylene glycol)—protein conjugates", 2003, Adv. Drug Del. Rev. 55: 1261-1277.

(56) References Cited

OTHER PUBLICATIONS

Tamaki et al., "PET in Oncology" Jpn J Cancer Clin, 2003, 49(6): 531-535.
Remington: The Science & Practice of Pharmacy, 21th Edition (Lippincott Williams & Wilkins, 2005) (book available on request).
Bendele et al., "Animal Models of Arthritis: Relevance to Human Disease", Toxicology Pathology, vol. 27, No. 1, pp. 134-142, 1999.
U.S. Appl. No. 60/956,489, filed Aug. 17, 2007, Low.
Leamon et al., "Folate-Liposome-Mediated Antisense Oligodeoxynucleotide Targeting to Cancer Cells: Evaluation in Vitro and in Vivo", Bioconjugate Chem., 14, 738-747, 2003.
Leamon et al., "Folate-mediated Drug Delivery: Effect of Alternative conjugate Chemistry", Journal of Drug Targeting, col. 7, No. 3, 157-169, 1999.
International Search Report and Written Opinion for PCT/US2007/023176 completed Aug. 4, 2008.
Tanaka, et al., "Digestive tract lesions and immunity," The Japanese Journal of Gastroenterology, 1994, vol. 91(2): 131-135.
Folate-FITC (http://www.medkoo.com/Anticancer-trials/EC-17.htm (downloaded on Aug. 8, 2013)).
Atherosclerosis (http://web.archive.org/web/20081207060136/http://en.wikipedia.org/wiki/Atheresclerosis (archived on Dec. 7, 2008).
Sudimack et al, Advanced Drug Delivery Reviews, 2000, 41: 147-162.
Yang et al, Imaging Tumor Folate Receptors using radiolabeled folate and methotrexate, Jour Labelled Compounds and Radiopharmaceuticals, 1999, Sussex, GB, vol. Suppl 1, 42: S696-S697.
Ilgan et al., "Imaging tumor folate receptors using 111IN-DTPA-methotrexate." Cancer Biother. Radiopharm., 1998, 13(3) pp. 177-184.
Akihiro H. et al., "Affinity for a-tocopherol transfer protein as a determinant of the biological activities of vitamin E analogs." Federation of European Biochemical Societies, 1997, vol. 409, pp. 105-108.
Kazui S. et al., "Novel vitamin D3 antipsoriatic antedrugs: 16-En-22-oxa-1a,25-(OH)2D3 analogs," Bioorganic & Medicinal Chemistry, 2006, vol. 14, pp. 1838-1850.
Hisashi T. et al., "c-Fos protein as a target of anti-osteoclastogenic action of vitamin D, and synthesis of new analogs," journal article, The Journal of Clinical Investigation, 2006, vol. 116, No. 2, February, pp. 528-535.
Masato S. et al., "Synthesis and biological activities of new 1a,25-dihydroxy-19-norvitamin D3 analogs with modifications in both the A-ring and the side chain," journal article, Bioorganic & Medicinal Chemistry, 2006, 14(12) pp. 4277-4294.
Agoston E.S. et al., "Vitamin D Analogs as Anti-Carcinogenic Agents" Anti-Cancer Agents in Medicinal Chemistry 2006, 6(1), pp. 53-71.
Lonsdale, D., "A Review of the Biochemistry, Metabolism and Clinical Benefits of Thiamin(e) and Its Derivatives." Evidence-Based Complementary & Alternative Medicine: eCAM. Advance Access Publication, vol. 3, Feb. 2006, pp. 49-59.
Nosaka, K. et al., "Separate Determination of Anticoccidial Thiamine Analogs by High-Performance Liquid Chromatography." ActaA Vitaminol. Et Enzymol., 1984, vol. 6 92), pp. 137-142.
Kandiko, C.T. et al., "Inhibition of Rat Brain Pyruvate Dehydrogenase by Thiamine Analogs." Biochem. Pharmacology, vol. 37, No. 22, (1988) pp. 4375-4380.
Spry, C. et al., "A Class of Pantothenic Acid Analogs Inhibits Plasmodium Falciparum Pantothenate Kinase and Represses the Proliferation of Malaria Parasites." Antimicrobial Agents and Chemotherapy, Nov. 2005, pp. 4649-4657.
Sargent, D.R. et al., "Antimetabolites of Pantothenic Acid, Ureido- and Carbamoyl-Derivatives." Texas Reports on Biology and Medicine, 1975, vol. 33, No. 3, pp. 433-443.
Hanck, A.B. et al., "Dexpanthenol (Ro 01-4709) in the treatment of constipation." Abstract, Acta Vitaminol Enzymol, 1982, vol. 4 (1-2), pp. 87-97.

Kagechika, H. et al., "Synthetic Retinoids: Recent Developments Concerning Structure and Clinical Utility." J. Med. Chem., Sep. 22, 2005, vol. 48, No. 19, pp. 5875-5883.
Shealy, Y.F. "Synthesis and Evaluation of Some New Retinoids for Cancer Chemoprevention." Preventive Medicine, 1989, vol. 18, pp. 624-645.
Landuer, W. et al., "The Interaction in Teratogenic Activity of the Two Niacin Analogs 3-acetylpyridine and 6-aminonicotinamide," J Experimental Zoology, 1962, vol. 151, pp. 253-258.
Renz, P. et al., "Synthesis of 4-Aza-5, 6-diethylbenzimidazole and Biosynthetic Preparation of 4- and 7-Aza-5,6-dimethylbenzimidazolylcobamide," Z. Naturforsch, 1997, vol. 52C, pp. 5287-5291.
Ayers, W.A., "Effect of Vitamin B12 and Analogs on the Respiration of a Marine Bacterium." Archives of Biochemistry and Biophysics, 1962, vol. 96, pp. 210-215.
Toraya, T. et al., "Immobilized Derivatives of Vitamin B12 Coenzyme and Its Analogs." Methods in Enzymology, 1980, vol. 67, pp. 57-66.
Ueda, M. et al., "Effect of Vitamin B12 Derivatives on Urinary Excretion of Methylmalonic Acid in Liver Diseases." Acta Med. Okayama, 1970, vol. 24, pp. 365-372.
Toraya, T. et al., "The Synthesis of Several Immobilized Derivatives of Vitamin B12 Coenzyme and Their Use as Affinity Adsorbents for a Study of Interactions of Diol Dehydrase with the Coenzyme." Journal of Biological Chemistry, 1980, vol. 255, No. 8, Apr. 25, pp. 3520-3525.
Takahata, Y. et al., "Synthesis, Properties and Microbiological Activity of Hydrophobic Derivatives of Vitamin B12." J. Nutr. Sci. Vitaminol., 1995, vol. 14, pp. 515-526.
Kamao, M. et al., "Determination of Plasma Vitamin K by High Performance Liquid Chromatography with Fluorescence Detection Using Vitamin K Analogs as Internal Standards." J. of Chromatography B., 2005, vol. 816, pp. 41-48.
Nishikawa, Y. et al., "Growth Inhibition of Hepatoma Cells Induced by Vitamin K and Its Analogs." Journal of Biological Chemistry, 1995, vol. 270, No. 47, Nov. 24, pp. 28304-28310.
Mack, D.O. et al., "The Carboxylation Activity of Vitamin K Analogs with Substitutions at Position 2, 3, or 5." Journal of Biological Chemistry, 1979, vol. 254, Apr. 25, pp. 2656-2664.
Mock, D.M. et al., "Urinary Biotin Analogs Increase in Humans During Chronic Supplementation: the Analogs are Biotin Metabolites." The American Physiological Society, 1997, pp. 83-85.
International Search Report for PCT/US2002/13890 completed Oct. 28, 2002.
Vesely, D.L. et al., "Biotin Analogs Activate Guanylate Cyclase." Molecular and Cellular Biochemistry, 1984, vol. 60, pp. 109-114.
Lambooy, J.P., "Riboflavin Analogs Utilized for Metabolism by a Lactobacillus casei Mutant." Int. J. Biochem., 1984, vol. 16, No. 2, pp. 231-234.
Nielsen, P. et al., "Phosphates of Riboflavin and Riboflavin Analogs: a Reinvestigation by High-Performance Liquid Chromatography." Analytical Biochemistry, 1983, vol. 130, pp. 359-368.
Arya, P. et al., "Design and Synthesis of Analogs of Vitamin E: Antiproliferative Activity Against Human Breast Adenocarcinoma Cells." Bioorganic & Medicinal Chemistry Letters, 1998, vol. 8, No. 18, pp. 2433-2438.
Trachewsky, D. "Antihypertensive Effect of Riboflavin Analogs in Rats with Mineralocorticoid-Induced Hypertension." Hypertension, 1981, vol. 3, No. 1, Jan-Feb., pp. 75-80.
Skinner, W.A. et al., "Structure-Activity Relations in the Vitamin E Series. II. Derivatives of alpha-Tocopherol Substituted at the 5-Methyl Group." J Med. Chem., 1962, vol. 12, pp. 64-66.
Neuzil, J. et al., "Vitamin E. Analogs: A New Class of Multiple Action Agents with Anti-Neoplastic and Anti-Atherogenic Activity." Apoptosis, 2002, vol. 7, pp. 179-187.
Politis, I. et al., "The Effect of Various Vitamin E Derivatives on the Urokinase-Plasmogen Activator System of Ovine Macrophages and Neutrophils." British Journal of Nutrition, 2003, vol. 89, pp. 259-265.

(56) References Cited

OTHER PUBLICATIONS

Wang, X. et al., "Vitamin E Analogs Trigger Apoptosis in HER2/erbB2-Overexpressing Breast Cancer Cells by Signaling Via the Mitochondrial Pathway." *Biochemical and Biophysical Research Communication*, 2005, vol.
Kilbourn et al, Fluorine-18 labeling of proteins, 1987, J Nucl Med, 28: 462-470.
Coussens et al, Inflammation and cancer, 2002, Nature, 420: 860-867.
PCT International Search Report and Written Opinion for PCT Application No. PCT/US2010/026406, mailed Apr. 15, 2010.
Jallad et al, Dissertation Abstracts International, 2001, 65(5B), p. 2390.
Stummer et al, J Neurosurg, 2000, 93:1003-1013.
Kennedy et al, Dissertation Abstracts International, 2001, 65(5B), p. 2354.
Nisshoshi, 1994, The Japanese Journal of Gastoenterology, 91(2): 131-135.
Extended European Search Report for EP 02734139, completed Jun. 11, 2004.
International PCT Search Report and Written Opinon for PCT Application No. PCT/US2008/053293, completed Mar. 10, 2009.
International PCT Search Report and Written Opinon for PCT Application No. PCT/US2005/046708, completed Sep. 20, 2006.
Extended European Search Report for EP 05855293, completed Jun. 12, 2009.
Extended European Search Report for EP 04753487, completed Jun. 16, 2006.
International PCT Search Report and Written Opinon for PCT Application No. PCT/US2004/016667, completed Sep. 22, 2004.
International PCT Search Report and Written Opinon for PCT Application No. PCT/US2008/064711, completed May 19, 2010.
International PCT Search Report and Written Opinon for PCT Application No. PCT/US2006/037112, completed Nov. 14, 2007.
Reddy J A et al: "Expression and functional characterization of the beta-isoform of the folate receptor on CD34(+) cells," Blood, vol. 93, No. 11, Jun. 1, 1999, pp. 3940-3948, XP002300805.
Japanese Translation of PCT International Application No. 2005-519078.
Japanese Translation of PCT International Application No. 2004-530678.
Extended European Search Report for EP 07867348, completed Jul. 29, 2010.

\* cited by examiner

TECHNETIUM-99m-EC20 NUCLEAR SCINTIGRAM

EC11 (Pte-L-γGlu-L-γGlu-L-βDpr-L-Asp-L-Cys)

EC13 (Pte-L-γGlu-L-βDpr-L-Ser-L-Cys)

EC14 (Pte-L-γGlu-D-γGlu-L-βDpr-L-Asp-L-Cys)

EC15 (Pte-L-γGlu-L-Cys-L-Asp-L-Cys)

EC19 (Pte-L-γGlu-L-βDpr-L-Asp-L-Cys)

EC20 (Pte-D-γGlu-L-βDpr-L-Asp-L-Cys)

EC31 (Pte-L-βDpr-L-Asp-L-Cys)

EC53 (Pte-D-γGlu-D-βDpr-D-Asp-D-Cys)

A

B

METHOD OF IMAGING LOCALIZED INFECTIONS

CROSS REFERENCE TO RELATED APPLICATION

This application is a U.S. national counterpart application of international application serial no. PCT/US2008/064711 filed May 23, 2008, which claims the benefit of priority under 35 U.S.C. §119(e) of U.S. provisional patent application Ser. No. 60/931,753 filed May 25, 2007, the disclosure of which are incorporated herein by reference in their entirety.

FIELD OF THE INVENTION

The invention relates to a method for targeting an imaging agent to cells of an animal to detect localized infections. More particularly, localized infections are detected by targeting imaging agents to inflammatory cells having receptors for a ligand, such as by using vitamin-imaging agent conjugates.

BACKGROUND AND SUMMARY OF THE INVENTION

Traditional methods for diagnosing infectious diseases rely on microscopic visualization of pathogens in a patient body fluid or tissue sample or the growth of the microorganism in the laboratory with the subsequent identification of the microorganism using clinical diagnostic tests. These techniques are generally reliable but are often time-consuming. Additionally, conventional methods of diagnosis, such as physical examinations, X-ray, CT scans, and ultrasonography, often fail to identify the location and/or the extent of infection in sites of localized infection (e.g., an abscess). Identifying the site of a localized infection and determining the extent of infection is important because rapid localization and rapid determination of the extent of an infection is critical to effective therapeutic intervention. If left untreated, infections can damage host tissue, or can become chronic. Infections can also become systemic by entering the bloodstream leading to sepsis, which is a serious, rapidly progressive, multi-organ disease state. Infections can also become gangrenous, resulting in loss of an infected limb, or even death.

An inflammatory response is one of the first responses to infection. Inflammation results in increased blood flow to the area of infection, release of chemicals (e.g., chemoattractants) to attract leukocytes to the site of infection, and migration of immune cells, such as monocytes and macrophages, to the site of infection as a defense against the invading microorganisms. Inflammation can be initiated by production of eicosanoids and cytokines, which are released by injured or infected cells. Eicosanoids include prostoglandins which promote fever and dilate blood vessels during an inflammatory response, and leukotrienes which attract certain leukocytes to the site of infection, including monocytes and macrophages.

Monocytes and macrophages are vital to the regulation of immune responses and to the development of an inflammatory response. As part of the innate immune system, macrophages and monocytes are continuously monitoring the tissues in which they are located and thus play a major role when bacteria are encountered. Specifically, macrophages have the ability to recognize pathogen-associated molecular patterns through their surface receptors (e.g. toll-like receptors) and help orchestrate the secretion of pro-inflammatory cytokines and other mediators, as well as engage in the direct phagocytosis of the invading microorganism. Common cytokines that are involved in inflammation include interlerkins responsible for communication between white blood cells, and chemokines that promote chemotaxis during an inflammatory response. Cytokines both recruit immune cells to the site of infection and cause immune cell activation during an inflammatory response.

Folate receptors are expressed on a subset of macrophages (i.e., activated macrophages), and on monocytes. Monocytes and macrophages participate in the immune response by non-specifically engulfing and killing foreign pathogens, by displaying degraded peptides from foreign proteins on their cell surfaces where they can be recognized by other immune cells, and by secreting cytokines and other factors that modulate the function of T and B lymphocytes, resulting in further stimulation of immune responses.

The overexpression of folate receptors on activated macrophages, and on monocytes, is described in U.S. Patent Application Publication No. US-2007-0009434-A1 and U.S. Patent Application Publication No. US-2002-0192157-A1, both of which are incorporated herein by reference. Additionally, compounds and methods for targeting radionuclide-based imaging agents to cells expressing the folate receptor are described in U.S. Pat. No. 7,128,893, incorporated herein by reference. Furthermore, compositions and methods for diagnosing and monitoring, using positron emission tomography, pathogenic disease states wherein the pathogenic cells uniquely express, preferentially express, or overexpress vitamin receptors are described in PCT Publication No. WO 2006/071754, incorporated herein by reference.

In one embodiment, a method is provided of detecting a site of localized infection by imaging a population of inflammatory cells, said method comprising the steps of administering to an animal suffering from an infection an effective amount of a composition comprising a conjugate of the formula $A_b$-X wherein the group $A_b$ comprises a vitamin and the group X comprises an imaging agent, and detecting the site of localized infection. In this embodiment, group X can further comprise a liposome, the vitamin can be selected from the group consisting of folate, riboflavin, thiamine, vitamin $B_{12}$, and biotin, the imaging agent can comprise a metal chelating moiety, the imaging agent can further comprise a metal cation, the metal cation can be a radionuclide, the radionuclide can be selected from the group consisting of isotopes of gallium, indium, copper, technetium, and rhenium, the composition can be administered parenterally to the animal, and the imaging method can be selected from the group consisting of computed tomography, positron emission tomography, magnetic resonance imaging, ultrasound, and single photon emission computed tomography, or a combination thereof.

In yet another embodiment an imaging method is provided for detecting localized infections. The method comprises the steps of administering to the patient a composition comprising a conjugate $A_b$-X which has the formula

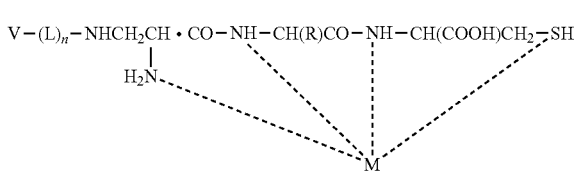

or

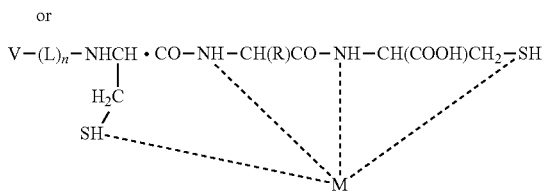

wherein V is a vitamin, L is a divalent linker, R is a side chain of an amino acid, M is a cation of a radionuclide, and n is 1, and detecting the site of the localized infection. In this embodiment, V can be a vitamin selected from the group consisting of folate, riboflavin, thiamine, vitamin $B_{12}$, and biotin, the radionuclide can be selected from the group consisting of isotopes of gallium, indium, copper, technetium, and rhenium, the composition can be administered parenterally to the animal, and the imaging method can be performed by a method selected from single photon emission computed tomography and computed tomography, or a combination thereof.

DETAILED DESCRIPTION OF THE INVENTION

Figure 1A:
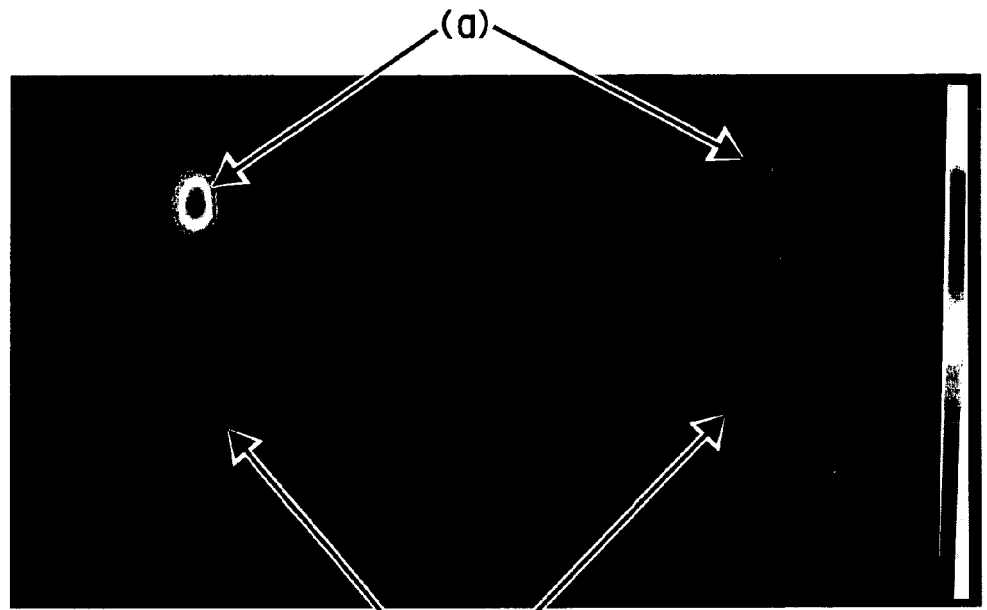
FIGS. 1A and 1B show images of a localized infection (i.e., an abscess) in the right thigh of each of two mice detectable using EC20. The abscess is shown in the left side of FIG. 1A and the left side of FIG. 1B. EC20 binding to inflammatory cells in the abscess area was competed with a 100-fold excess of unlabeled folic acid (right side of FIG. 1A and right side of FIG. 1B). The designations (a) and (b) indicate the thigh and tail sections of the mice, respectively.

While the invention is susceptible to various modifications and alternative forms, illustrative embodiments are described herein. It should be understood, however, that there is no intent to limit the invention to the particular forms described, but on the contrary, the intention is to cover all modifications, equivalents, and alternatives falling within the spirit and scope of the invention.

In one embodiment, the invention relates to a method of detecting a site of localized infection by imaging a population of inflammatory cells, said method comprising the steps of administering to an animal suffering from an infection an effective amount of a composition comprising a conjugate of the formula $A_b$-X wherein the group $A_b$ comprises a vitamin and the group X comprises an imaging agent, and detecting the site of localized infection. In this embodiment, other illustrative aspects include embodiments where the group X further comprises a liposome, the vitamin is selected from the group consisting of folate, riboflavin, thiamine, vitamin $B_{12}$, and biotin, the imaging agent comprises a metal chelating moiety, the imaging agent further comprises a metal cation, the metal cation is a radionuclide, the radionuclide is selected from the group consisting of isotopes of gallium, indium, copper, technetium, and rhenium, the composition is administered parenterally to the animal, and the imaging method is selected from the group consisting of computed tomography, positron emission tomography, magnetic resonance imaging, ultrasound, and single photon emission computed tomography, or a combination thereof.

In yet another embodiment an imaging method is provided for detecting localized infections. The method comprises the steps of administering to the patient a composition comprising a conjugate $A_b$-X which has the formula

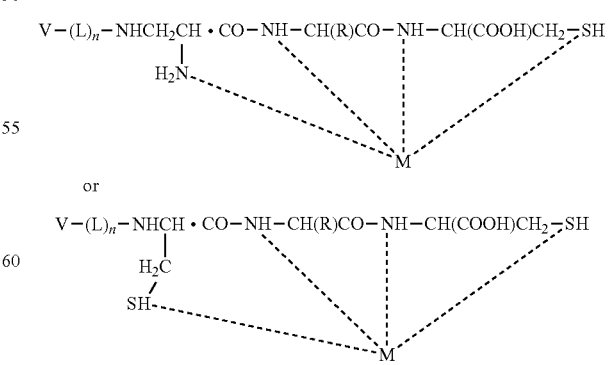

wherein V is a vitamin, L is a divalent linker, R is a side chain of an amino acid, M is a cation of a radionuclide, and n is 1, and detecting the site of the localized infection. In this embodiment, other illustrative aspects include embodiments where V is a vitamin selected from the group consisting of folate, riboflavin, thiamine, vitamin $B_{12}$, and biotin, the radionuclide is selected from the group consisting of isotopes of gallium, indium, copper, technetium, and rhenium, the composition is administered parenterally to the animal, and the imaging method is performed by a method selected from single photon emission computed tomography and computed tomography, or a combination thereof.

An infection results from the presence of one or more pathogenic microbial agents in a host. For example, these pathogenic microbial agents may include viruses, bacteria, fungi, protozoa, multicellular parasites, prions, or other microorganisms. An infection may be caused by any type of pathogenic microbial agent, and these microbial agents may come from the environment or may already be present in the host's body fluids or tissue. For example, *Staphylococcus* species are present naturally on skin where they generally remain harmless to the host. However, when *Staphylococcus* species enter a normally sterile environment, e.g. the capsule of a joint or the peritoneum, they can multiply, leading to an infection in the host. Depending on the causal agents involved, an infection may start in any part of the body.

In accordance with the invention, any type of localized infection caused by a microorganism and transmitted in any manner may be detected by the methods described herein. In accordance with the invention, a "localized infection" means an infection occurring predominantly in a specific part of the body, and that is detectable in a specific part of the body using the methods described herein. An example of a "localized infection" is an abscess, but the term "localized infection" is not limited to any specific type of infection.

In accordance with the invention "ligand-imaging agent conjugate" means a conjugate of an imaging agent and any ligand that can be used to target an inflammatory cell. In accordance with the invention "vitamin-imaging agent conjugate" means a conjugate of an imaging agent and any vitamin that can be used to target an inflammatory cell.

The method described herein can be used for both human clinical medicine and veterinary applications. Thus, the animal afflicted with the localized infection can be a human, or in the case of veterinary applications, can be a laboratory, agricultural, domestic, or wild animal.

In one embodiment, the ligand-imaging agent conjugates, such as vitamin-imaging agent conjugates, are administered parenterally to the animal suffering from the localized infection, for example, intradermally, subcutaneously, intramuscularly, intraperitoneally, intrathecally, or intravenously. In an alternate embodiment, the conjugates can be administered to the animal by other medically useful procedures and any effective dose and suitable dosage form can be used, including oral dosage forms, and effective doses can be administered in standard or prolonged release dosage forms, such as by using a slow pump.

Examples of parenteral dosage forms include aqueous solutions of the conjugate in well-known pharmaceutically acceptable liquid carriers such as liquid alcohols, glycols (e.g., polyethylene glycols), glucose solutions (e.g., 5%), esters, amides, sterile water, buffered saline (including buffers like phosphate or acetate; e.g., isotonic saline). Additional exemplary components include vegetable oils, gelatin, lactose, amylose, magnesium stearate, talc, silicic acid, paraffin, and the like. In another aspect, the parenteral dosage form can be in the form of a reconstitutable lyophilizate comprising one or more doses of the conjugate. In various aspects, solubilizing agents, local anaesthetics (e.g., lidocaine), excipients, preservatives, stabilizers, wetting agents, emulsifiers, salts, and lubricants can be used. In one aspect, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference.

In one illustrative aspect, a localized infection can be detected by administering to an animal suffering from a localized infection an effective amount of a composition comprising a conjugate of the general formula $A_b$-X wherein the group $A_b$ comprises a ligand, such as a vitamin, capable of binding to inflammatory cells, and the group X comprises an imaging agent, and thereafter scanning the animal with an imaging device capable of detecting the imaging agent.

In one embodiment, the localized infection is detected by imaging a population of activated macrophages that express a receptor for a vitamin. In another embodiment, the localized infection is detected by imaging other types of inflammatory cells that express a receptor for a vitamin, such as monocytes, progenitor cells, or other types of inflammatory cells involved in localized infections.

In one illustrative embodiment, the conjugates are administered as a composition comprising a conjugate and a pharmaceutically acceptable carrier. In one illustrative aspect, the composition is formulated for parenteral administration and is administered to the animal in an amount effective for imaging of the site of the localized infection due to the presence and concentration of inflammatory cells, detectable by using the conjugates, at the site of the localized infection.

The nature of the imaging agent component of the conjugate is dictated by the imaging methodology. Thus, in various illustrative embodiments, the imaging agent can comprise a chelating moiety and a metal cation, for example, a radionuclide, detectable by scintigraphy, or a nuclear resonance imaging contrast agent, such as gadolinium. In other illustrative embodiments, the imaging agent can be an imaging agent suitable for computed tomography, positron emission tomography, magnetic resonance imaging, ultrasound, or single photon emission computed tomography, or a combination thereof.

Compositions and methods for using positron emission tomography are described in PCT Publication No. WO 2006/071754, incorporated herein by reference. For positron emission tomography (PET), an extra-corporeal device is used. PET detection using an extra-corporeal device is also referred to as a "PET scan," and devices for extra-corporeal detection using PET are well known in the art. In another embodiment, compounds and methods for targeting radionuclide-based imaging agents to cells is described in U.S. Pat. No. 7,128,893, incorporated herein by reference, and these compounds and methods can be used in the method described herein. In another embodiment, the imaging agent can be a fluorophore and methods and compositions useful for imaging using a fluorophore conjugated to a ligand, such as a vitamin, are described in U.S. Patent Application Publication No. US-2007-0009434-A1, and U.S. Patent Application Publication No. US-2002-0192157-A1, both of which are incorporated herein by reference. In various embodiments, fluorophores can include fluorescein, Oregon Green (e.g., 514 and 488), rhodamine, phycoerythrin, Texas Red, AlexaFluor 488, AlexaFluor 647, DYLIGHT 680, and infrared imaging agents.

In one embodiment, the conjugate is administered to the animal, and following a period of time to allow delivery and concentration of the imaging agent at the site of the localized infection, the animal is subjected to the imaging method. In one embodiment, for example, the method comprises the step of performing an imaging procedure about 1 hour to about 6 hours post-administration of the conjugate.

In one embodiment, the group $A_b$ in the conjugates of the formula $A_b$-X, can be a ligand capable of binding to activated macrophages. Any of a wide number of macrophage-binding ligands can be employed. In illustrative embodiments, such ligands include N-formyl peptides (e.g., f-Met-Leu-Phe), high mobility group factor 1 protein (HMGB1), hyaluronan fragments, HSP-70, toll-like receptor ligands, scavenger receptor ligands, co-receptors for antigen presentation, ligands that bind to the CD68, BER-MAG3, RFD7, CD4, CD14, and HLA-D markers on activated macrophages, ligands that bind to urokinase plasminogen activator receptors (e.g., the WX-360 peptide), antibodies, or fragments thereof, that bind preferentially to activated macrophages, and vitamins or receptor-binding vitamin analogs.

In other embodiments, for monocytes, a monocyte-binding ligand can be used as the group $A_b$. The monocyte-binding ligands can include CD40-, CD16-, CD14-, CD11b-, and CD62-binding ligands, 5-hydroxytryptamine, macrophage inflammatory protein 1-α, MIP-2, receptor activator of nuclear factor kB ligand antagonists, monocyte chemotactic protein 1-binding ligands, chemokine receptor 5-binding ligands, RANTES-binding ligands, chemokine receptor-binding ligands, and vitamins or receptor-binding vitamin analogs/derivatives, and the like.

In one embodiment, the conjugates are capable of preferentially binding to activated monocytes or activated macrophages compared to resting monocytes or macrophages due to preferential expression of the receptor for the ligand on activated monocytes or macrophages. Exemplary of such ligands are vitamins.

Acceptable vitamin moieties that can be used in accordance with the invention include niacin, pantothenic acid, folic acid, riboflavin, thiamine, biotin, vitamin $B_{12}$, and the lipid soluble vitamins A, D, E and K. In one embodiment, these vitamins, and their receptor-binding analogs, constitute the group $A_b$ that can be coupled with the group X to form the conjugates for use in accordance with the invention. Exemplary vitamin moieties are described in U.S. Pat. No. 5,688,488, incorporated herein by reference. Exemplary of a vitamin analog is a folate analog containing a glutamic acid residue in the D configuration (folic acid normally contains one glutamic acid in the L configuration linked to pteroic acid).

In illustrative embodiments, acceptable ligands include folate, and analogs of folate, where the folate analogs bind to the folate receptor, and antibodies or antibody fragments capable of recognizing and specifically binding to surface moieties uniquely or preferentially expressed or presented in/on inflammatory cells, such as the folate receptor. In one embodiment, the activated macrophage binding ligand is folic acid, or a folic acid analog that binds to the folate receptor. Activated macrophages express a 38 kDa GPI-anchored folate receptor that binds folate with subnanomolar affinity (i.e., <1 nM). In another embodiment, the activated macrophage binding ligand is a specific monoclonal or polyclonal antibody or Fab or scFv (i.e., a single chain variable region) fragment of an antibody capable of specific binding to activated macrophages, e.g. through binding to the folate receptor.

In one embodiment, the vitamin can be folic acid, a folic acid analog, or another folate receptor-binding molecule. In various illustrative embodiments, analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), pemetrexed, pralatrexate, $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). A folate receptor-binding ligand includes folate, folate analogs, and other folate receptor binding molecules in accordance with this invention.

In another embodiment the folate analog used has the formula

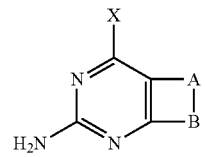

wherein X' is hydroxyl or amino;
-A-B— is —W'=C(R)—CH=W²—, —C(R)=CH—N(R²)—, or —W¹=C(R)—S—, where R² is hydrogen or alkyl;
W¹ and W² are each independently selected from the group consisting of N and C(R¹), where R¹ is in each instance independently selected from the group consisting of hydrogen, alkyl, fluoro and chloro;
R is

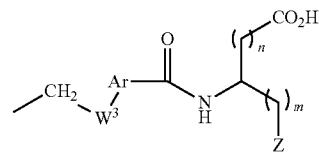

wherein n is 0 to 2; m is 1 to about 4; Z is $NH_2$ or $CO_2H$;
W³ is O, S, N(R³) or CHR³; where R³ is hydrogen, methyl, alkyl, alkenyl, alkynyl or cyanoalkyl; and
Ar is an optionally substituted divalent linker selected from the group consisting of 1,4-phenylene, 2,5-pyridylene, 3,6-pyridylene; 2,4-thiazolylene, 2,5-thiazolylene, 2,5-thienylene, 2,5-imidazolylene, 3,6-pyridinzylene and 2,5-pyrazinylene.

In another embodiment the folate analog used has the formula

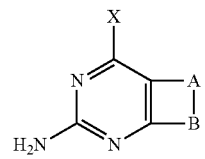

wherein $X^1$ is hydroxyl or amino;

-A-B— is —$W^1$=C(R)—CH=$W^2$—, —C(R)=CH—N($R^2$)—, or —$W^1$=C(R)—S—; where $R^2$ is hydrogen or alkyl;

$W^1$ and $W^2$ are each independently selected from the group consisting of N and C($R^1$); where $R^1$ is in each instance independently selected from the group consisting of hydrogen, alkyl, fluoro and chloro;

R is

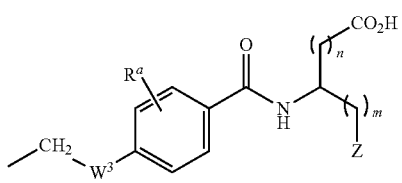

wherein n is 0 to 2; m is 1 to about 4; Z is $NH_2$ or $CO_2H$; $W^3$ is O, S, N($R^3$) or $CHR^3$; where $R^3$ is hydrogen, methyl, alkyl, alkenyl, alkynyl or cyanoalkyl; and $R^a$ is from zero to three substituents independently selected from fluoro, chloro, alkyl or haloalkyl.

In other embodiments, the imaging agent can be conjugated with multiple, different vitamins, or vitamin receptor binding analogs, to enhance the opportunity for binding to the respective cell membrane receptors. Alternatively, independent portions of the dose of a vitamin-imaging agent conjugate can constitute different vitamin-imaging agent conjugates to enhance the opportunity for binding to the respective cell membrane receptors.

In embodiments where the group $A_b$ is folic acid, a folic acid analog, or another folic acid receptor binding ligand, methods for conjugating folic acid, folic acid analogs, or other folic acid receptor binding ligands, to imaging agents are described in detail in U.S. Pat. Nos. 5,688,488, 5,416,016, and 5,108,921, and 7,128,893, each incorporated herein by reference in its entirety.

In various embodiments, the group $A_b$ may be conjugated to the group X (i.e., the imaging agent) by using any art-recognized method for forming a complex. In illustrative embodiments, this can include covalent, ionic, or hydrogen bonding of the group $A_b$ to the group X, either directly or indirectly via a linking group such as a divalent linker. In one illustrative aspect, the conjugate is formed by covalent bonding of the group $A_b$ to the imaging agent through the formation of amide, ester or imino bonds between acid, aldehyde, hydroxy, amino, or hydrazo groups on the respective components of the conjugate. Methods of linking ligands to imaging agents are described in PCT Publication No. WO 2006/012527, incorporated herein be reference. In one embodiment, a linker can comprise an indirect means for associating the group $A_b$ with the group X, such as by connection through spacer arms or bridging molecules.

In addition, in various embodiments structural modifications of the linker portion of the conjugates are made. For example, a number of amino acid substitutions may be made to the linker portion of the conjugate, including but not limited to naturally occurring amino acids, as well as those available from conventional synthetic methods. In one aspect, beta, gamma, and longer chain amino acids may be used in place of one or more alpha amino acids. In another aspect, the stereochemistry of the chiral centers found in such molecules may be selected to form various mixtures of optical purity of the entire molecule, or only of a subset of the chiral centers present. In another aspect, the length of the peptide chain included in the linker may be shortened or lengthened, either by changing the number of amino acids included therein, or by including more or fewer beta, gamma, or longer chain amino acids. In another aspect, the selection of amino acid side chains in the peptide portion may be made to increase or decrease the relative hydrophilicity of the linker portion specifically, or of the overall molecule generally.

Similarly, the length and shape of other chemical fragments of the linkers described herein may be modified. In one aspect, the linker includes an alkylene chain. The alkylene chain may vary in length, or may include branched groups, or may include a cyclic portion, which may be in line or spiro relative to the alkylene chain.

In one embodiment the group $A_b$ is folic acid, an analog of folic acid, or any other folate receptor binding molecule, and the folate ligand is conjugated to the imaging agent by a procedure that utilizes trifluoroacetic anhydride to prepare γ-esters of folic acid via a pteroyl azide intermediate. This procedure results in the synthesis of a folate ligand, conjugated to the imaging agent only through the γ-carboxy group of the glutamic acid groups of folate. In other embodiments, folate or folic acid analogs can be coupled through the α-carboxy moiety of the glutamic acid group or both the α and γ carboxylic acid entities.

In another illustrative embodiment, a carboxylic acid on a vitamin moiety or on the imaging agent can be activated using carbonyldiimidazole or standard carbodiimide coupling reagents such as 1-ethyl-3-(3-dimethylaminopropyl)-carbodiimide (EDC) and thereafter reacted with the other component of the conjugate, or with a linker, having at least one nucleophilic group, viz hydroxy, amino, hydrazo, or thiol, to form the vitamin-imaging agent conjugate coupled, with or without a linker, through ester, amide, or thioester bonds.

As discussed above, the conjugate $A_b$-X can be formed by a chemical linkage in the conjugate that is a direct linkage or the linkage can be through an intermediary linker. In illustrative embodiments, an intermediary linker can be any biocompatible linker known in the art. In one embodiment, the linker comprises about 1 to about 30 carbon atoms, more typically about 2 to about 20 carbon atoms. In another embodiment, lower molecular weight linkers (i.e., those having an approximate molecular weight of about 30 to about 500) are employed. In illustrative aspects, any linkers or linking methods or chemistry known in the art can also be used.

In illustrative embodiments, the imaging agent may comprise benzamidyl, benzylic, or phenyl groups, other aromatic groups, such as, for example, naphthyl and benzoxazolyl groups, and the like. By appropriate selection, linkers may limit the rate of excretion of the conjugate from the animal by permitting the targeting group, $A_b$, to associate with the appropriate receptor on inflammatory cells before being excreted in the bile from the liver, or in the urine. A linker may facilitate, or may delay metabolic consumption of the conjugate such as by retarding reticuloendothelial system uptake, particularly by the liver. A linker may also help avoid association of the conjugate with non-target organs, cells, fluids, or proteins. Also, the linker may help facilitate or accelerate a preferred route of excretion of the conjugate, such as through urine, for example, by encouraging the animal (e.g., a human patient) to drink significant fluids after the administration of the conjugate.

In the method described herein, an imaging agent is used. In one embodiment, a compound that emits radiation can be used. In one embodiment, the imaging agent is useful in positron emission tomography (i.e., a compound that emits positron radiation capable of producing a pair of annihilation photons moving in opposite directions, the annihilation photons being produced as a result of positron annihilation with an electron). In this embodiment, the imaging agent typically comprises a radioisotope linked to another chemical structure (e.g., a benzene ring) to form the imaging agent. However, the imaging agent can comprise the radioisotope alone. Such positron-emitting compounds are described in PCT Publication No. WO 2006/071754, incorporated herein by reference.

In one embodiment, the imaging agent may include a positron-emitting isotope having a suitable half-life and toxicity profile. In various embodiments, the positron-emitting isotope has a half-life of more than 30 minutes, more than 70 minutes, more than 80 minutes, more than 90 minutes, more than 100 minutes, less than 8 hours, less than 6 hours, less than 4 hours, or less than 3 hours. In other embodiments, the radioisotope has a half-life of about 30 minutes to about 4 hours, about 70 minutes to about 4 hours, about 80 minutes to about 4 hours, about 90 minutes to about 4 hours, about 100 minutes to about 4 hours, about 30 minutes to about 6 hours, about 70 minutes to about 6 hours, about 80 minutes to about 6 hours, about 90 minutes to about 6 hours, about 100 minutes to about 6 hours, about 30 minutes to about 8 hours, about 70 minutes to about 8 hours, about 80 minutes to about 8 hours, about 90 minutes to about 8 hours, or about 100 minutes to about 8 hours.

In various embodiments, the positron-emitting isotope is selected from group consisting of $^{34}$Cl, $^{45}$Ti, $^{51}$Mn, $^{61}$Cu, $^{63}$Zn, $^{68}$Ga, $^{11}$C, $^{13}$N, $^{15}$O, and $^{18}$F. In one illustrative embodiment, the isotope is $^{18}$F.

In another embodiment, compounds and methods for targeting radionuclide-based imaging agents to cells are described in U.S. Pat. No. 7,128,893, incorporated herein by reference, and these compounds and methods can be used in the method described herein (see Examples 2-5). In this embodiment, an imaging method is provided for detecting localized infections. The method comprises the steps of administering to an animal a composition comprising a conjugate $A_b$-X which has the formula

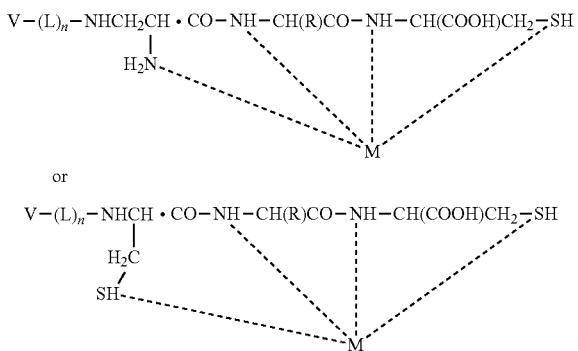

wherein V is a vitamin, L is a divalent linker, R is a side chain of an amino acid, M is a cation of a radionuclide, and n is 1, and detecting the site of the localized infection. In this embodiment, V can be a vitamin selected from the group consisting of folate, riboflavin, thiamine, vitamin $B_{12}$, and biotin, the radionuclide can be selected from the group consisting of isotopes of gallium, indium, copper, technetium, and rhenium, the composition can be administered parenterally to the animal, and the imaging method can be performed, for example, by a method selected from single photon emission computed tomography and computed tomography, or a combination thereof.

Illustrative radionuclides suitable for diagnostic imaging include radioisotopes of gallium, indium, copper, technetium and rhenium, including isotopes $^{111}$In, $^{99m}$Tc, $^{64}$Cu, $^{67}$Cu, $^{67}$Ga or $^{68}$Ga. These radionuclides are cationic and are complexed with the chelator through the chelating group of the conjugate to form the vitamin-imaging agent conjugate according to methods described in Examples 4 and 5 and in Leamon et al. *Bioconjug. Chem.*, vol. 13, pp. 1200-1210 (2002), incorporated herein by reference. Exemplary vitamin-imaging agent conjugates for use in the method described herein are shown in FIG. 3 and include EC11, EC13, EC14, EC15, EC19, EC20, EC31, and EC53.

The compositions for use in the method described herein comprise an amount of the ligand-imaging agent conjugate, such as a vitamin-imaging agent conjugate, effective to visualize sites of localized infection when administered in one or more doses. The amount of the conjugate effective for use in accordance with the invention depends on many parameters, including the nature of the infection, the molecular weight of the conjugate, its route of administration, and the possibility of co-usage of other diagnostic and/or monitoring agents. The effective amount to be administered to an animal, such as a human patient, is typically based on body surface area, weight and physician assessment of condition. For example, an effective amount can range from about 1 ng/kg to about 1 mg/kg, more typically from about 1 µg/kg to about 500 µg/kg, and most typically from about 1 µg/kg to about 100 µg/kg. In other embodiments, the vitamin-imaging agent conjugate can be administered in combination with about 0.5 ng/kg to about 100 mg/kg, or about 1 µg/kg to about 100 mg/kg, or about 100 µg/kg to about 100 mg/kg of the unlabeled vitamin. "In combination with" means that the unlabeled vitamin can be either co-administered with the conjugate or the unlabeled vitamin can be preinjected before administration of the conjugate to improve image quality.

In various illustrative aspects, any effective regimen for administering the composition containing the ligand-imaging agent conjugate, such as a vitamin-imaging agent conjugate, can be used. For example, the composition can be administered as a single dose, or it can be administered in multiple doses, if necessary, to achieve visualization of the site of localized infection. Additional injections of the composition containing the ligand-imaging agent conjugate, such as a vitamin-imaging agent conjugate, can be administered to the animal at an interval of days or months after the initial injections(s), and the additional injections can be useful for monitoring the progress of the infection.

Example 1

Materials

Figure 4:
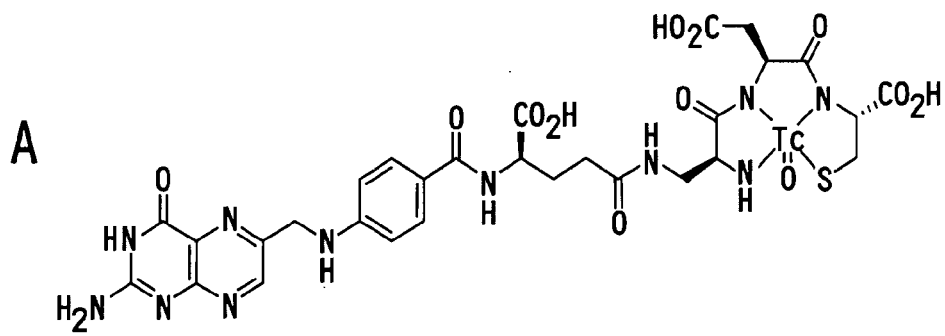
FIG. 4 shows the structure of the folate imaging agent, EC-20 (Panel A) and an experimental protocol for EC-20 based imaging of bacterial infections (Panel B).
Figure 4:
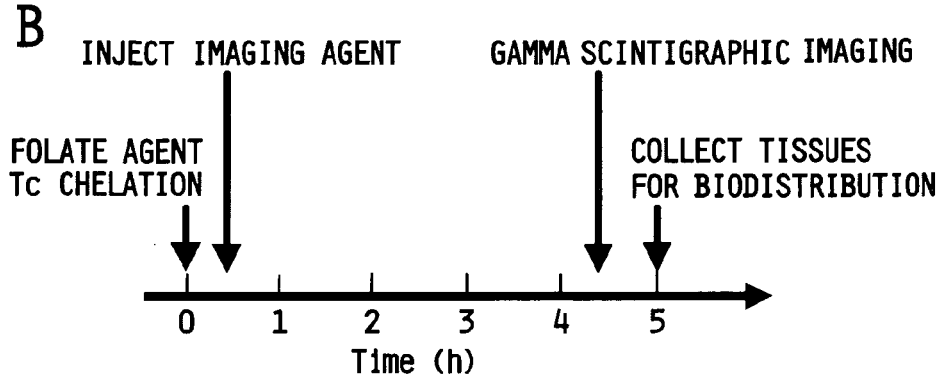

EC-20 (a folate-linked chelator of $^{99m}$Tc), was obtained from Endocyte Inc. (West Lafayette, Ind.). EC-20, a low molecular weight (745.2 Da) folate based chelating agent, possesses and rapid radioactive labeling, high binding affinity ($K_d$~3 nM) to its target receptor, rapid clearance (I.V. plasma $t_{1/2}$~4 min), and has minimal side effects. The conjugate consists of a folate targeting ligand tethered to a peptide chelating moiety via a short 2 carbon spacer (FIG. 4). After simple on-site $^{99m}$Tc labeling, EC-20 imaging can be accomplished in as little as 4 h post injection making this diagnostic agent highly amenable to most clinical settings.

$^{99m}$Tc-labeled sodium pertechnetate was purchased from Cardinal Health Services (Indianapolis, Ind.). Folic acid and Sephadex G-10 beads were purchased from Sigma/Aldrich (St. Louis, Mo.). Tryptic soy agar (BD 236950) and tryptic soy broth (BD 211825) were purchased from Becton, Dickinson and Company (Franklin Lakes, N.J.). *Staphylococcus aureus* (ATCC #BAA-934) was purchased from the American Type Culture Collection (Manassas, Va.). TriColor-conjugated monoclonal antibody against mouse F4/80 was purchased from CALTAG (Invitrogen) and folate Oregon green was synthesized as previously described in U.S. Appl. Publ. No. 20070009434. Six-eight week old male Balb/c mice were obtained from Harlan (Indianapolis, Ind.) and housed/used in accordance with Purdue University animal care/use guidelines.

Example 2

Maintenance of Bacterial Cultures

*Staphylococcus aureus* (*S. aureus*) BAA-934 was propagated according to the protocol supplied by the American Type Culture Collection (ATCC). Briefly, cultures were grown on tryptic soy agar plates or in broth at 37° C. for 24 hours. Tryptic soy culture plates were stored at 2-5° C. for further use. Bacterial enumeratation was based on $OD_{600}$ measurements. Bacteria were grown to an $OD_{600}$ of about 1 to about 2 overnight and used directly in tryptic soy broth. Proper Biosafety level 2 guidelines were followed in accordance with CDC and Purdue Biosafety protocols.

Example 3

Animal Models of *S. Aureus* Infection

Infection was induced in either the cuadal muscular (thigh) or flank region in Balb/c (~20 g) mice as previously described. See Bettegowda, et al. *Proc. Natl. Acad. Sci. U.S.A.*, vol. 102, pp. 1145-1150 (2005) and Bunce, et al. *Infect. Immun.*, vol. 60, pp. 2636-2640 (1992), each incorporated herein by reference. Briefly, on day one, about $2.5 \times 10^6$ CFU to about $1 \times 10^7$ CFU (based on optical density) of *S. aureus* in 50 µL in tryptic soy broth containing 0.08 g/mL G10 Sephadex beads was injected in the posterior right caudal muscular region (thigh) of the mouse. For induction of the flank model, $10^7$ CFU in 200 µL of tryptic soy agar (containing 0.08 g/mL G10 Sephadex beads) was injected subcutaneously in the right flank. Animals developed abscesses detectable as palpable masses within 24-48 h after inoculation. Animals were given ad libitum access to standard mouse chow and water throughout the course of the study and monitored on a daily basis to assess their heath status.

Example 4

Scintigraphic Imaging of Mice

Figure 1B:
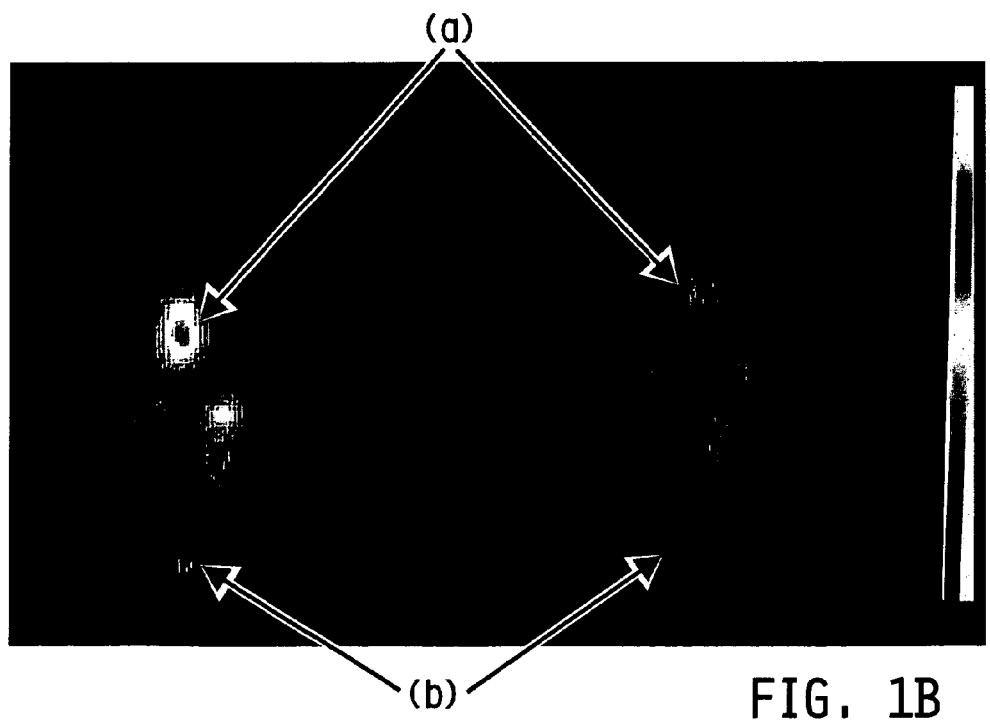

EC20 chelation of Tc was performed as previously described without modification. See Leamon et al. *Bioconjug. Chem.*, vol. 13, pp. 1200-1210 (2002), incorporated herein by reference. Four days after induction of infection, mice were injected intraperitoneally with 1 mCi (37 MBq; 0.006 mg per mouse) of EC20 or 1 mCi (37 MBq) of EC-20 plus a 100-fold to 200-fold molar excess of folic acid (adjusted to pH=7.4). Four hours later, mice underwent nuclear imaging using either a Medical Imaging Electronics (Elk Grove Village, Il) gamma scintigraphy instrument equipped with ProcessX imaging software or a Kodak 4000 Imaging workstation equipped with Kodak 1D molecular imaging software. For scintigraphic evaluation using the Medical Imaging Electronics instrument, image acquisition was performed for 5 minutes while images were acquired for 20 seconds using the Kodak imaging station. Gamma emission from the abdomen and thorax was shielded using 1 8-inch lead plates. Alternatively, tissues possessing the abscess were surgically removed from the mouse and imaged as described above. As shown in FIGS. 1, A and B, an abscess in the right thigh of each mouse tested was detectable using EC20 (left side of FIGS. 1, A and B). EC20 binding was competed with a 100-fold excess of unlabeled folic acid (see right side of FIGS. 1, A and B).

Figure 6:
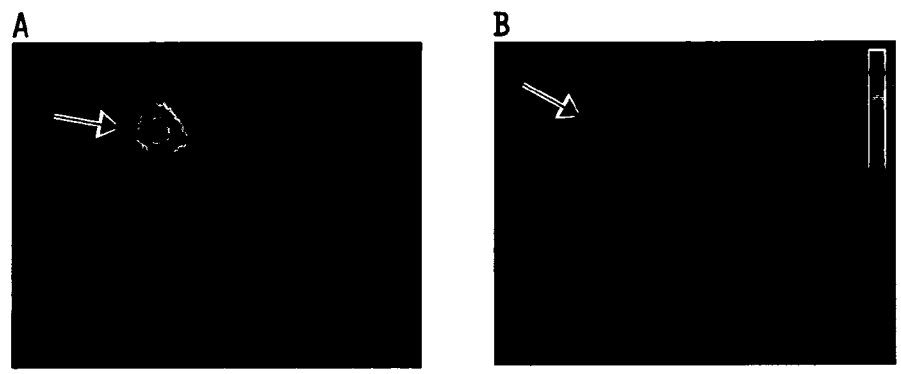
FIG. 6 shows representative standard gamma scintigraphic images demonstrating EC-20 uptake in mice infected with. S. aureus. Mice were infected with $10^7$ CFU of S. aureus (indicated by arrows) in the thigh region of the right leg. Four days later, mice were dosed IP with 37 MBq EC-20 (Panel A) or 37 MBq EC-20 with a 200-fold excess of free folic acid (Panel B) and imaged. Competition (Panel B) confirmed folate mediated uptake of EC-20.

In vivo gamma scintigraphic imaging using the folate $^{99m}$Tc imaging probe, EC-20, confirmed selective uptake of the folate radiotracer at the *S. aureus* infection site (FIG. 6, Panel A). Furthermore, intense uptake was confined to a focal region in the right thigh without other sites observed in the right leg or in the uninfected left control limb. Control mice infected in the same manner were administered a 200-fold excess of folic acid (competed control group) to verify folate mediated targeting of the imaging agent to the site of infection. Accordingly, very little uptake of the EC-20 imaging agent was noted in the right thigh region in the control mice and indicated saturation of FR with folic acid thereby preventing folate radiotracer uptake (FIG. 6, Panel B). A total of 24 mice (12 pairs) were imaged using this protocol. Region of interest (ROI) counts were determined and demonstrated a significant difference (P<0.0001, n=12) between mouse groups (infected right limbs, non-completed vs. infected right limbs, competed). Moreover, a second analysis between right infected limbs and left non-infected limbs in the non-competed infection group showed a significant difference (P<0.0001, n=12). The signal from the kidney and bladder was blocked with a ⅛ inch thick lead shield to prevent image saturation as previously described.

Example 5

Scintigraphic Imaging of Horses

Figure 2:
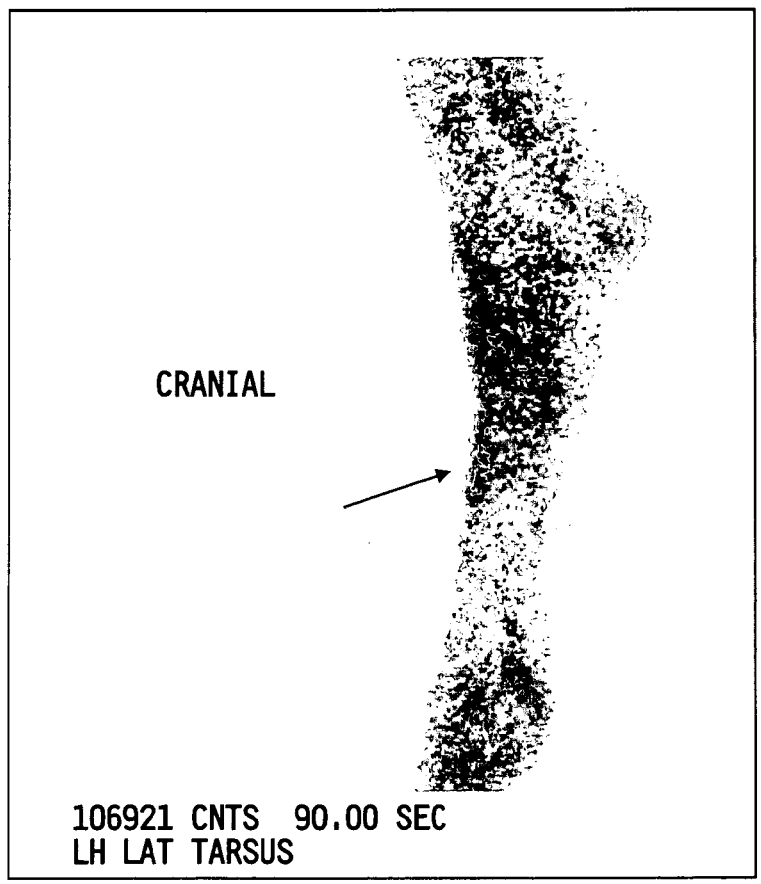
FIG. 2 shows an image of a localized infection in the limb of a horse using technetium-99m-EC20 detected using nuclear scintigraphy. Lateral acquisition of the left hindlimb (90 second) was performed. The site of infection is the dark spot shown with the arrow.
Figure 3A:
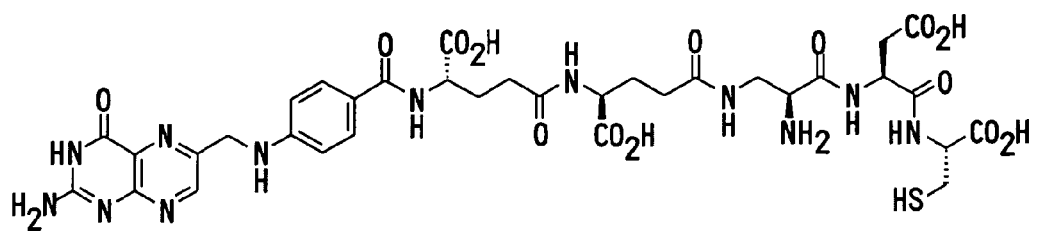
FIG. 3 shows structures of EC11, EC13, EC14, EC15, EC19, EC20, EC31, and EC53.
Figure 3A:
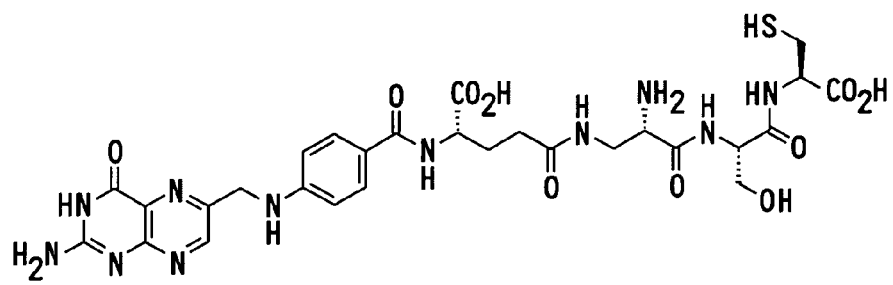
Figure 3A:
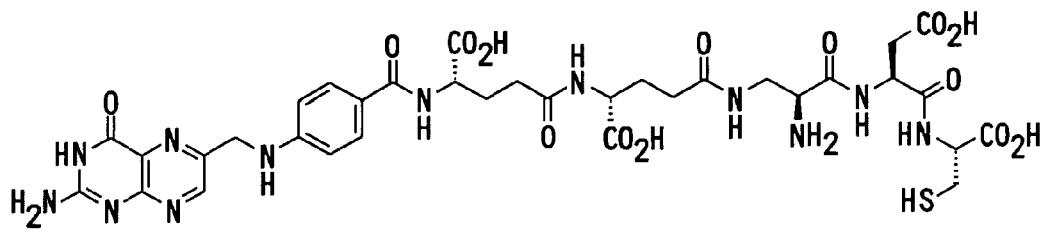
Figure 3B:
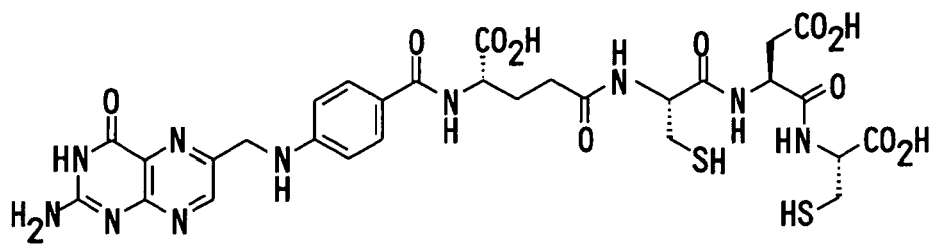
Figure 3B:
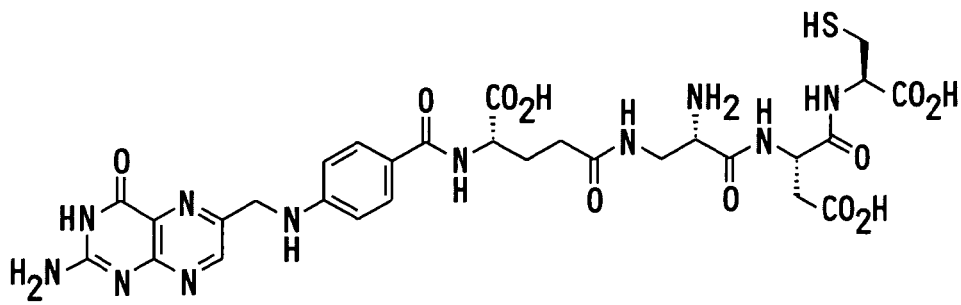
Figure 3B:
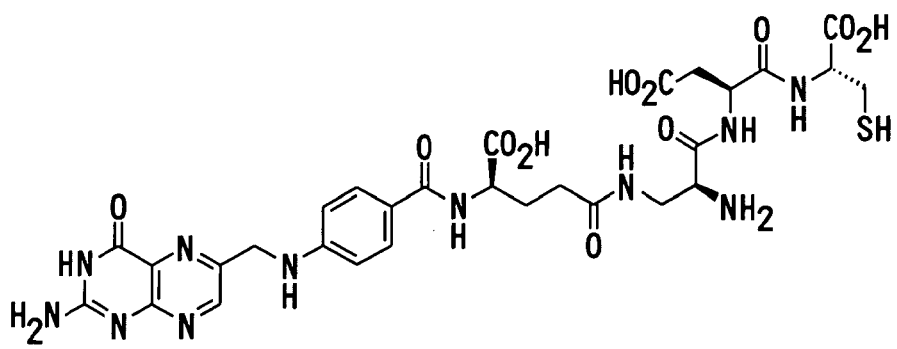
Figure 3C:
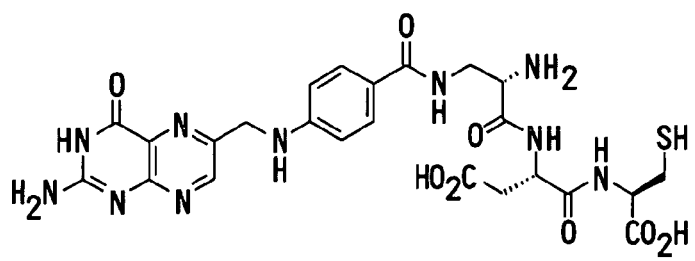
Figure 3C:
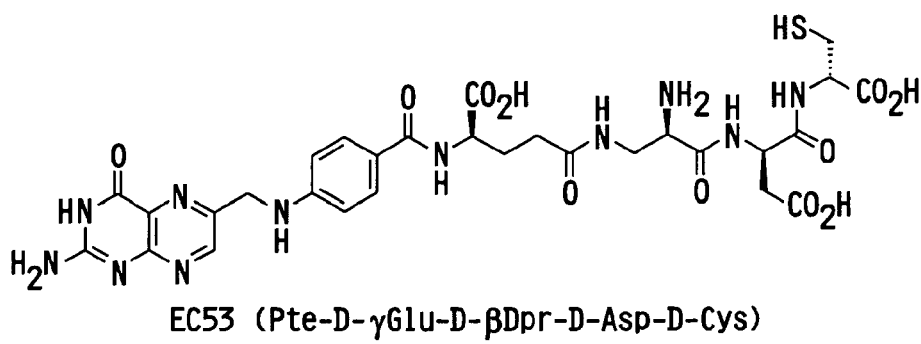

The horse presented with a 3-day history of severe cellulitis of the left hind limb. She was grade IV/V lame in the left hind limb. The swelling extended from the coronary band to the stifle joint. The limb had severe pitting edema with no apparent wounds or draining tracts. Standard radiography of the limb revealed no apparent bony abnormalities. Nuclear scintigraphy was performed using a gamma camera. Technetium-99m chelated to EC20 (as described above) was used to identify possible areas of inflammation within the edematous limb. The animal received 145 mCi of technetium-99m and 1 mg of EC20. A 90 second lateral acquisition of the left hind limb from the distal tibia to the proximal metatarsal III was performed 4 hours after intravenous injection of the radioisotope. There was increased radioisotope uptake along the superficial dorsal border of the proximal metatarsal III. After completion of the nuclear scintigraphy, the horse was sedated and a scalpel blade was used to incise the skin along the dorsal proximal metatarsal III. A subcutaneous abscess of purulent debris was identified at that location which had previously been identified with gamma scintigraphy (see FIG. 2).

Example 6

Flow Cytometric Analysis of FR+ Macrophages

IN INFECTED MICE *S. aureus*-recruited macrophages were isolated 4 days after I.P. injection of $1 \times 10^6$ CFU of live *S. aureus* in 200 uL tryptic soy agar via peritoneal lavage (8 mL of PBS) Cells were washed with PBS twice and resuspended in folate deficient RPMI. Cell suspensions were incubated with the appropriate antibodies for 30 minutes on ice. Samples were washed 3× in PBS followed by incubation with folate Oregon green (100 nM) for 30 min at 37° C. In some cases, cells were co-incubated with 10 µM folic acid to competitively block all FR. In all experiments, appropriate isotype controls were used. Flow cytometry was performed using a BD FACSCalibur flow cytometer and CELLQUEST software (Becton Dickinson, San Jose, Calif.) for acquisition and analysis as previously described.

Figure 5:
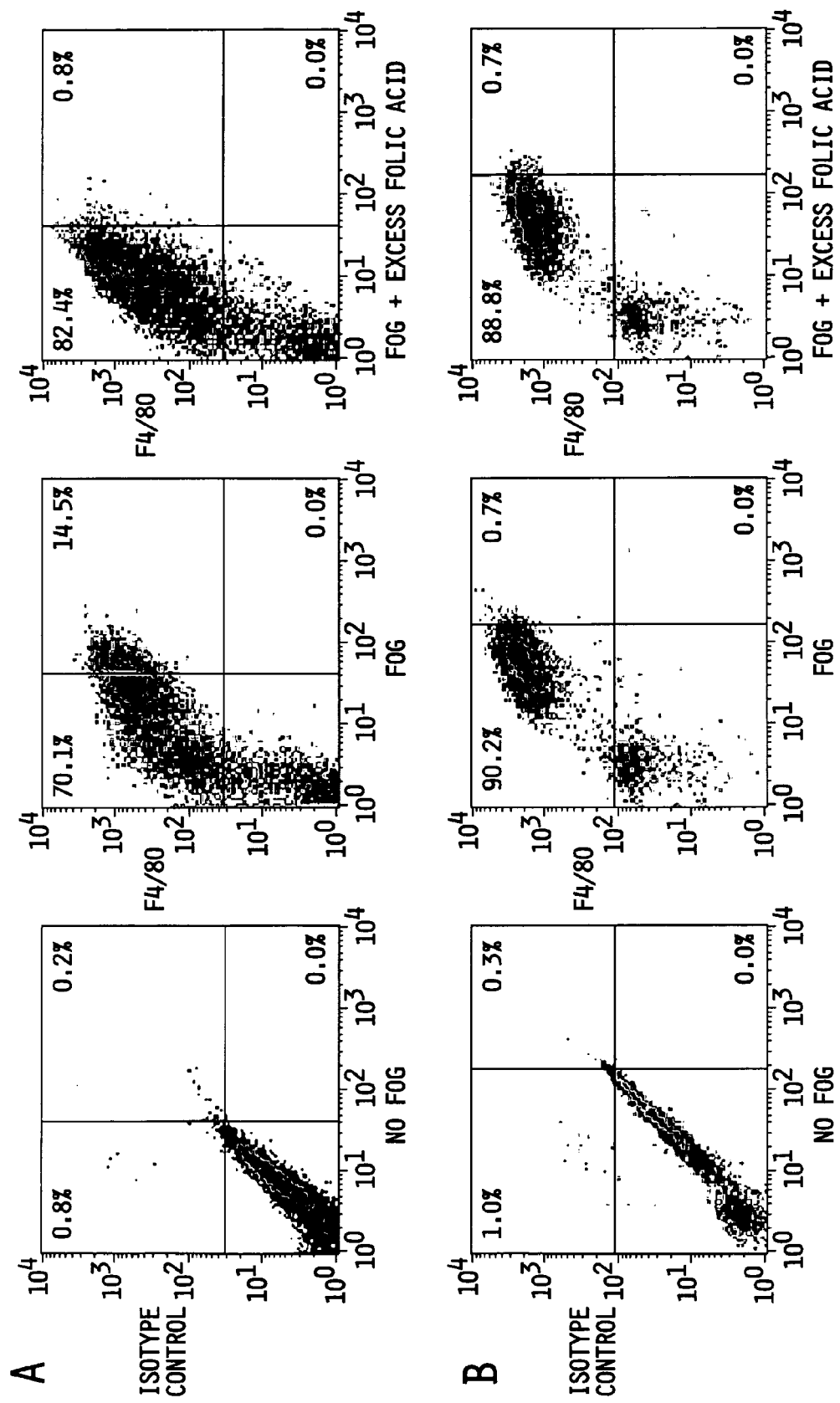
FIG. 5 shows the expression of folate receptors on F4/80+ macrophages recruited by S. aureus. Cells isolated from the peritoneal cavity of mice injected with either S. aureus (Panel A) or sterile saline (Panel B) were analyzed by flow cytometry. To demonstrate that folate-Oregon green (FOG) binding is mediated by the folate receptor (FR) the same cell isolates were co-incubated with 1000-fold molar excess of folic acid and examined by flow cytometry (far right panels). The percentage of macrophages co-stained with the F4/80 macrophage marker and FOG are indicated in each respective quadrant.

To confirm the presence of FR positive macrophages during S. aureus infections, mice were infected I.P. with S. aureus and peritoneal cells were harvested by lavage 4 days post-infection. The cell suspension was then treated with folate-Oregon green plus a murine macrophage-specific antibody, anti-F4/80, and analyzed by flow cytometry for folate conjugate binding. As seen in FIG. 5, Panel A middle panel, a subpopulation of the peritoneal macrophages (F4/80+ cells) bound high levels of Folate-Oregon green. Further, folate-Oregon green uptake by the macrophage was quantitatively inhibited by a 1000-fold excess free folic acid (FIG. 5, Panel A, right panel), which indicated that folate-Oregon green binding to these cells was FR-specific. Resting F4/80+ macrophages isolated from non-infected control mice expressed low levels of FR (FIG. 5, Panel B).

Example 7

Spatially Co-Registered Radioisotopic, Radiographic and Reflectance Imaging

General preparation of the mice for imaging was performed as described above. All experiments were performed on a Kodak In Vivo FX imaging station. Spatially co-registered images, image acquisition, optimization, and overlays were performed using Kodak Molecular Imaging Software v. 4.5.1. All images had a focus setting of 7 mm to match the distance of the animal imaging chamber above the platen, and the field of view was set to 20×20 cm (100 microns/pixel). For reflectance mode, images were acquired for 0.05 s using a white illumination source, no emission filter, and an f-stop ring setting of 11. Radioisotopic images were acquired for 20 s using a Kodak radioisotopic phosphor screen (cat. #8527715) with no illumination source, binning set to 4×4, and an f-stop ring setting of 0. Radiographic images were acquired for 240 s using a Kodak radiographic phosphor screen (cat. #8509051) with no light source. X-ray images were acquired with the following settings: energy of 35 KVP, current of 149 µA, 0.5 mm X-ray filter and an f-stop ring setting of 4. These settings were minor modifications of standard methods recommended by the manufacturer.

Figure 7:
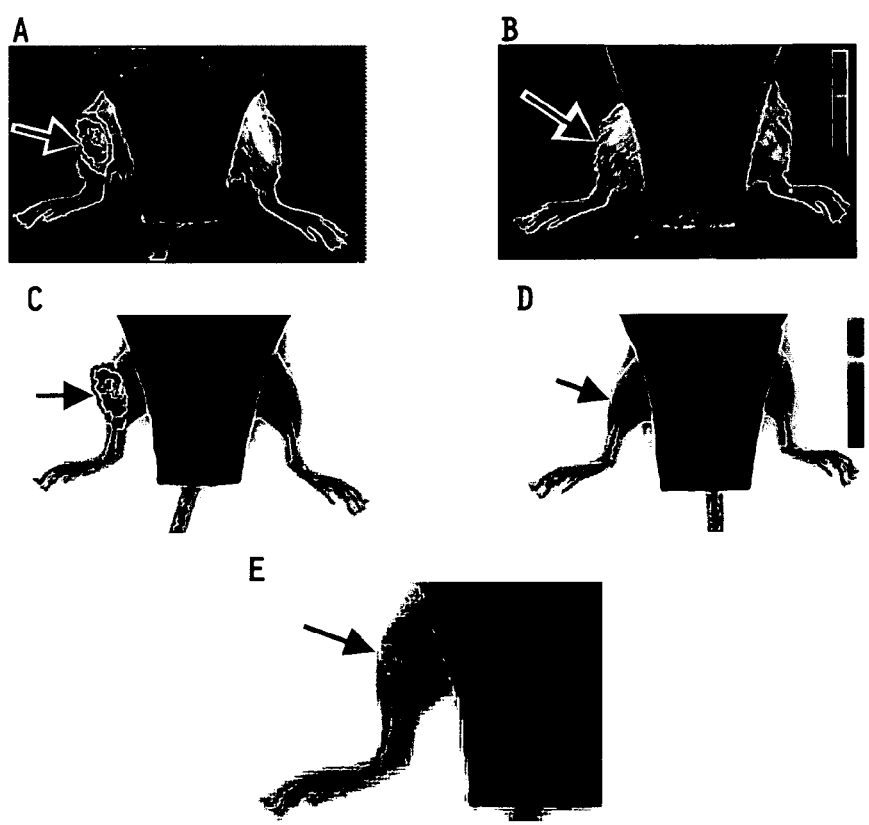
FIG. 7 shows representative radioisotopic images demonstrating EC-20 uptake in mice infected with. S. aureus (site of injection indicated by arrows) co-registered with both reflective and radiographic images. Mice were infected with $10^7$ CFU S. aureus and dosed IP with 37 MBq EC-20 identically as described for standard gamma scintigraphy (Panels A and C: co-registered reflective image) or 37 MBq EC-20 with a 200-fold excess of free folic acid (Panels B and D: co-registered radiographic image) and imaged in the ventral recumbancy position 4 h later. Using the imaging software, the saturation was adjusted to define the area of highest radioisotopic uptake (Panel E).

Additional imaging of S. aureus infected mice was performed using a Kodak imaging workstation, which allowed co-registration of both reflectance and radiographic images with the radioisotopic images. FIG. 7 (Panels A and B) shows the reflective image with the corresponding radioisotopic overlay and FIG. 7 (Panels C and D) demonstrate the radioisotopic overlay of the radiographic image. Uptake was limited to the right thigh region (indicated in arrow) with the radioisotopic images overlayed on both the reflectance and the radiographic images and was consistent with the standard gamma scintigraphic images previously acquired. When the image intensity was adjusted to define only the most intense region, the site of infection foci was localized to the site of initial infection based upon radiographic anatomical landmarks (FIG. 7, Panel E). Further enhancement of signal intensity via the imaging software enabled clear visualization of the infection focus. As with gamma scintigraphic imaging, a ⅛ lead cut-out was used to shield both the bladder and kidney to prevent signal saturation.

Example 8

Biodistribution of Ec-20

Six to eight week old male Balb/C mice (4 per group) were infected with $1 \times 10^7$ CFU of S. aureus in the thigh region as described above. On day four, mice were injected intraperitoneally with 37 MBq (0.006 mg per mouse) of EC20 or 37 MBq EC-20 plus a 200-fold molar excess of folic acid (adjusted to pH=7.4). After 4 h, mice were sacrificed and their respective tissues harvested, weighed and analyzed using a gamma counter (Packard BioScience, Meridin, Conn.). Results were expressed as percentage injected dose per gram of tissue (% ID/g).

Figure 8:
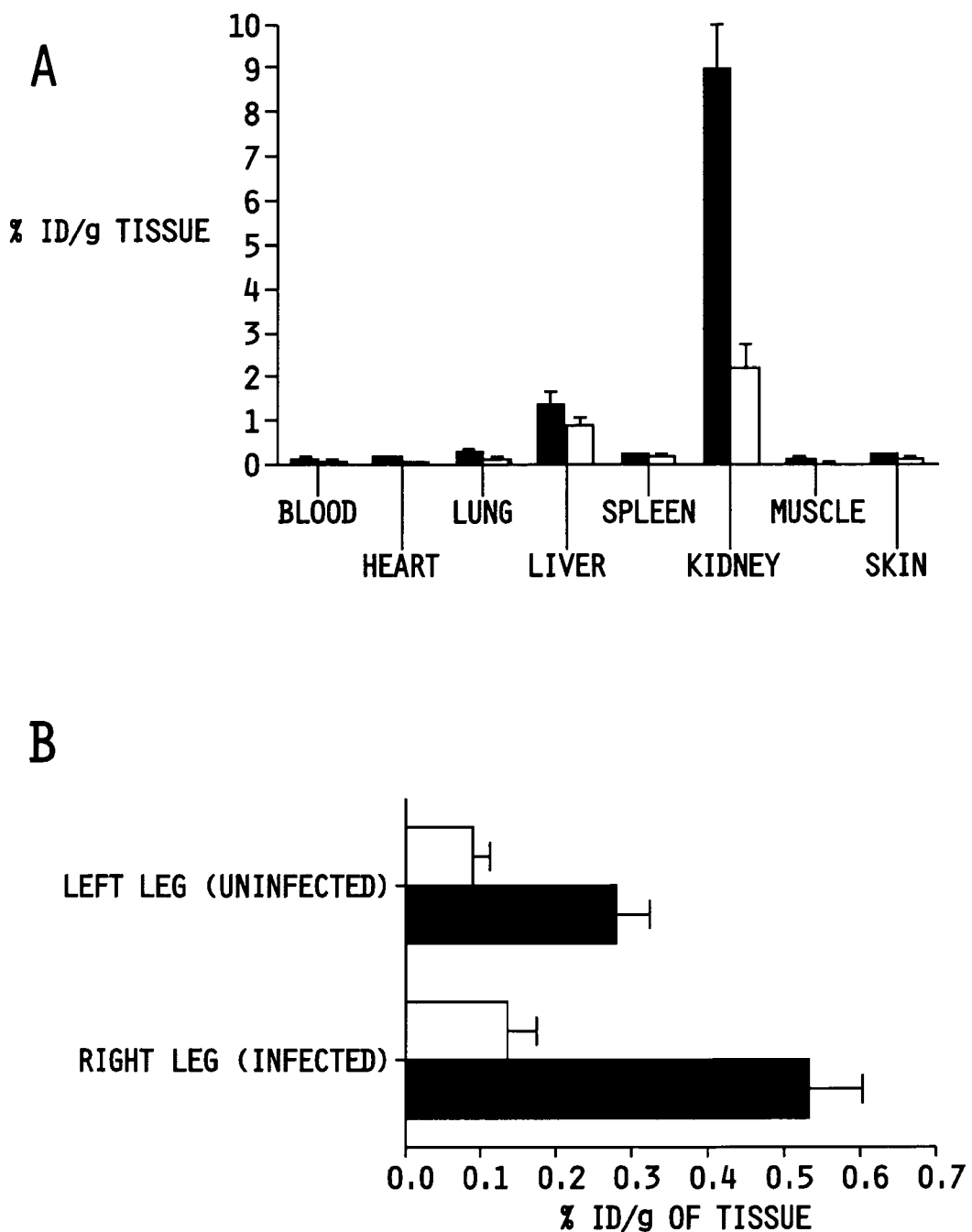
FIG. 8 shows the biodistribution (Panels A and B) of EC-20 in infected mice. Panel B represents uptake of the radio-tracer in both the infected and non-infected limbs. Black bars and white bars indicate infected mice and infected mice pre-dosed with a 200 fold excess of folic acid, respectively (n=4 per group, mean±SEM).

Biodistribution analysis (FIG. 8) confirmed major EC-20 uptake sites in the kidney, liver, and the infected right limb (8.97% ID/g, 1.38% ID/g, and 0.53% ID/g, respectively). Uptake in the kidney is primarily due to high FR expression, which appears to be necessary for transcytosis of folic acid back into the bloodstream; whereas, uptake in the liver is associated with resident FR+ macrophages. The next highest uptake was registered in the infected leg, which was consistent with the presence of FR+ macrophages localized at the site of the infection. Due to the inherent difficulty excising only the focal area in mice, the whole leg was used for the biodistribution analysis. Thus, the measured % ID/g of EC-20 in the leg represented both the infection foci as well non-infected tissue and bone, and therefore reduced sensitivity. A significant difference ($P<0.027$, $n=4$) was noted between the right (infected) limbs and the competed control limbs (mice administered EC-20 plus a 200 fold excess acid) and between the infected and non-infected limbs of the same animal ($P<0.013$, $n=4$).

Example 9

Statistical Methods

Statistical significance between groups was assessed using either the unpaired or paired (where appropriate) Student t-test. P values less than 0.05 were considered significant.

While certain embodiments of the present invention have been described and/or exemplified above, it is contemplated that considerable variation and modification thereof are possible. Accordingly, the present invention is not limited to the particular embodiments described and/or exemplified here.

What is claimed is:

1. A method for detecting an abscess in an animal, the method comprising the step of administering to the animal a composition comprising a conjugate of the formula $A_b$-X wherein the group $A_b$ comprises a folate receptor-binding ligand and the group X comprises an imaging agent, wherein the abscess is detected by imaging by binding of the conjugate to a population of monocytes or macrophages at the site of the abscess, and wherein the imaging is performed by positron emission tomography.

2. The method of claim 1 wherein the group X further comprises a liposome.

3. The method of claim 1 wherein the folate receptor-binding ligand is a folate.

4. The method of claim 1 wherein the imaging agent comprises a metal chelating moiety.

5. The method of claim 4 wherein the imaging agent further comprises a metal cation.

6. The method of claim 5 wherein the metal cation is a radionuclide.

7. The method of claim 6 wherein the radionuclide is selected from the group consisting of isotopes of gallium, indium, copper, technetium, and rhenium.

8. The method of claim 7 wherein the radionuclide is an isotope of technetium.

9. The method of claim 1 wherein the composition is in a parenteral dosage form.

10. The method of claim 3 wherein the folate receptor-binding ligand is folate.

11. The method of claim 1 wherein the animal is a human patient.

12. The method of claim 1 wherein the animal is a veterinary patient.

13. The method of claim 12 wherein the veterinary patient is a horse.

14. The method of claim 9 wherein the composition further comprises a pharmaceutically acceptable carrier.

15. The method of claim 14 wherein the pharmaceutically acceptable carrier is a liquid carrier.

16. The method of claim 9 wherein the parenteral dosage form is a reconstituted lyophilizate.

17. The method of claim 9 wherein the parenteral dosage form is selected from the group consisting of intradermal, subcutaneous, intramuscular, intraperitoneal, intravenous, and intrathecal dosage forms.

18. The method of claim 15 wherein the liquid carrier is selected from the group consisting of saline, glucose, alcohols, glycols, esters, amides, and a combination thereof.

19. The method of claim 1 wherein the composition further comprises a component selected from the group consisting of a solubilizing agent, a local anesthetic, an excipient, a preservative, a stabilizer, a wetting agent, an emulsifier, a salt, and a lubricant.

\* \* \* \* \*